US008227371B2

(12) United States Patent
Holtcamp et al.

(10) Patent No.: US 8,227,371 B2
(45) Date of Patent: Jul. 24, 2012

(54) CLASS OF OLEFIN METATHESIS CATALYSTS, METHODS OF PREPARATION, AND PROCESSES FOR THE USE THEREOF

(75) Inventors: Matthew W. Holtcamp, Huffman, TX (US); Matthew S. Bedoya, Humble, TX (US); Laughlin G. McCullough, League City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 12/890,315

(22) Filed: Sep. 24, 2010

(65) Prior Publication Data
US 2012/0077945 A1    Mar. 29, 2012

(51) Int. Cl.
C07F 11/00    (2006.01)
C07F 7/04    (2006.01)
B01J 31/00    (2006.01)

(52) U.S. Cl. .......... 502/152; 502/155; 556/59; 556/470; 556/482; 568/809; 568/814; 568/881; 548/101; 548/103

(58) Field of Classification Search .............. 502/152, 502/155; 556/59, 470, 482; 568/809, 814, 568/881; 548/101, 103
See application file for complete search history.

(56) References Cited

U.S. PATENT DOCUMENTS

| | | | |
|---|---|---|---|
| 5,182,405 A | 1/1993 | Arduengo, III | |
| 5,312,940 A | 5/1994 | Grubbs et al. | |
| 5,342,909 A | 8/1994 | Grubbs et al. | |
| 5,710,298 A | 1/1998 | Grubbs et al. | |
| 5,726,334 A | 3/1998 | Beatty et al. | |
| 5,728,839 A | 3/1998 | Herrmann et al. | |
| 5,728,917 A | 3/1998 | Grubbs et al. | |
| 5,750,815 A | 5/1998 | Grubbs et al. | |
| 5,831,108 A | 11/1998 | Grubbs et al. | |
| 5,840,238 A | 11/1998 | Setiabudi et al. | |
| 5,917,071 A | 6/1999 | Grubbs et al. | |
| 5,936,100 A | 8/1999 | Furstner et al. | |
| 6,001,909 A | 12/1999 | Setiabudi | |
| 6,025,496 A | 2/2000 | Herrmann et al. | |
| 6,100,323 A | 8/2000 | Setiabudi et al. | |
| 6,500,975 B1 | 12/2002 | Schwab et al. | |
| 6,613,910 B2 * | 9/2003 | Grubbs et al. ............ | 548/103 |
| 6,737,531 B1 * | 5/2004 | Dioumaev et al. ......... | 548/101 |
| 6,803,429 B2 | 10/2004 | Morgan et al. | |
| 7,119,216 B2 | 10/2006 | Newman et al. | |
| 7,205,424 B2 | 4/2007 | Nolan | |
| 7,268,242 B2 | 9/2007 | Pederson et al. | |
| 7,312,331 B2 | 12/2007 | Bertrand et al. | |
| 7,329,758 B1 | 2/2008 | Grubbs et al. | |
| 2003/0100782 A1 | 5/2003 | Grubbs et al. | |
| 2007/0043180 A1 | 2/2007 | Zhan | |

FOREIGN PATENT DOCUMENTS

| | | |
|---|---|---|
| WO | WO 97/20865 | 6/1997 |
| WO | WO 97/29135 | 8/1997 |
| WO | WO 2006/138166 | 12/2006 |
| WO | WO 2008/010961 | 1/2008 |
| WO | WO 2008/046106 | 4/2008 |
| WO | WO 2008/095785 | 8/2008 |
| WO | WO 2008/125568 | 10/2008 |
| WO | WO 2008/140468 | 11/2008 |

OTHER PUBLICATIONS

U.S. Appl. No. 61/025,076, filed Jan. 31, 2008.
U.S. Appl. No. 12/143,663, filed Jun. 20, 2008.
U.S. Appl. No. 61/203,523, filed Dec. 23, 2008.
U.S. Appl. No. 12/487,739, filed Jun. 19, 2009.
U.S. Appl. No. 12/488,066, filed Jun. 19, 2009.
U.S. Appl. No. 12/488,093, filed Jun. 19, 2009.
Alder, "Bis(diisopropylamino)carbene," Angew. Chem. Int. Ed., 1996, vol. 35, No. 10, pp. 1121-1128.
Anderson et al., "Synthesis and Reactivity of Olefin Metathesis Catalysts Bearing Cyclic (Alkyl)(Amino)Carbenes," Angew. Chem. Int. Ed., 2007, vol. 46, pp. 7262-7265.
Anderson et al., "Kinetic Selectivity of Olefin Metathesis Catalysts Bearing Cyclic (Alkyl)(Amino)Carbenes," Organometallics, 2008, vol. 27, pp. 563-566.
U.S. Appl. No. 61/259,514, filed Nov. 9, 2009.
U.S. Appl. No. 61/259,521, filed Nov. 9, 2009.
U.S. Appl. No. 12/705,136, filed Feb. 12, 2010.
U.S. Appl. No. 12/660,815, filed Mar. 4, 2010.
U.S. Appl. No. 61/314,388, filed Mar. 16, 2010.
U.S. Appl. No. 61/376,925, filed Aug. 25, 2010.
Belderrain et al., "Reaction between Ruthenium (0) Complexes and Dihalo Compounds. A New Method for the Synthesis of Ruthenium Olefin Metathesis Catalysts," Organometallics, 1997, vol. 16, No. 18, pp. 4001-4003.
Berlin et al., "Highly Active Chiral Ruthenium Catalysts for Asymmetric Cross- and Ring-Opening Cross-Metathesis," Angew. Chem. Int. Ed., 2006, vol. 45, pp. 7591-7595.
Bourissou et al., "Stable Carbenes," Chem. Rev., 2000, vol. 100, No. 1, pp. 39-91.
Burdett et al., "Renewal Monomer Feedstocks via Olefin Metathesis: Fundamental Mechanistic Studies of Methyl Oleate Ethenolysis with the First-Generation Grubbs Catalyst," Organometallics, 2004, vol. 23, No. 9, pp. 2027-2047.

(Continued)

Primary Examiner — Robert D. Harlan

(74) Attorney, Agent, or Firm — Renuka N. Ganesh; Catherine L. Bell

(57) ABSTRACT

This invention relates to a metathesis catalyst comprising (i) a Group 8 metal hydride-dihydrogen complex represented by the formula:

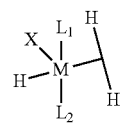

wherein M is a Group 8 metal; X is an anionic ligand; and $L_1$ and $L_2$ are neutral donor ligands; and (ii) a ligand exchange agent represented by the formula J-Y, wherein J is selected from the group consisting of hydrogen, a $C_1$ to $C_{30}$ hydrocarbyl, and a $C_1$ to $C_{30}$ substituted hydrocarbyl; and Y is selected from the group consisting of halides, alkoxides, aryloxides, and alkyl sulfonates.

51 Claims, 1 Drawing Sheet

OTHER PUBLICATIONS

Chaudret et al., "*Preparation of Polyhydride Complexes of Ruthenium by Direct Hydrogenation of Zerovalent Olefinic Derivatives. Mononuclear Complexes of the Type $RuH_6L_2$ and $RuH_4L_3$. Spontaneous H-D Exchange between the Phosphine Protons and the Solvent Catalyzed by $RuH_4L_3$*," Organometallics, 1985, vol. 4, No. 10, pp. 1722-1726.

Christ et al., "*Synthesis, Characterization, and Chemistry of a 16-Electron Dihydrogen Complexes of Ruthenium*," Organometallics, 1994, vol. 13, No. 10, pp. 3800-3804.

Crowe et al., "*Chain Transfer Agents for Living Ring-Opening Metathesis Polymerization Reactions of Norbornene*," Macromolecules, 1990, vol. 23, No. 14, pp. 3534-3536.

Cucullu et al., "*Catalytic Dehalogenation of Aryl Chlorides Mediated by Ruthenium (II) Phosphine Complexes*," Organometallics, 1999, vol. 18, No. 7, pp. 1299-1304.

Enders et al., "*Preparation, Structure, Reactivity of 1,3,4-Triphenyl-4,5-dihydro-1H-1,2,4-triazol-5-ylidene, a New Stable Carbene*," Angew. Chem. Int. Ed., 1995, vol. 34, No. 9, pp. 1021-1023.

Grant No. DE-FG36-04GO14016, "*Platform Chemicals from an Oilseed Biorefineiy*," awarded by the Department of Energy, Final Technical Report, Nov. 30, 2006.

Hermann et al., "*Nickel (II) Complexes of N-Heterocyclic Carbenes*," Organometallics, 1997, vol. 16, No. 10, pp. 2209-2212.

Hermann et al., "*N-Heterocyclic Carbenes*," Angew. Chem. Int. Ed., 1997, vol. 36, pp. 2163-2187.

Hermann et al., "*Heterocyclic Carbenes: [+] A High-Yielding Synthesis of Novel, Functionalized N-Heterocyclic Carbenes in Liquid Ammonia*," Chem. Eur. J., 1996, vol. 2, No. 12, pp. 1627-1635.

Herrmann et al., "*N-Heterocyclic Carbenes[+] : Generation under Mild Conditions and Formation of Group 8-10 Transition Metal Complexes Relevant to Catalysis*," Chem. Eur. J., 1996, vol. 2, No. 7, pp. 772-780.

Holmes et al., "*Some Reactions of Tungsten Methylidyne Complexes and the Crystal Structure of $[W_2(CPMe_3)_2(PMe_3)_4][-AlCl_4]_2$*," Organometallics, 1984, vol. 3, No. 3, pp. 476-484.

Jazzar et al., "*Intramolecular 'Hydroiminiumation' of Alkenes: Applications to the Synthesis of Conjugate Acids of Cyclic Alkyl Amino Carbenes (CAACs)*," Angew. Chem. Int. Ed., 2007, vol. 46, No. 16, pp. 2899-2902.

Jazzar et al., "*A New Synthetic Method for the Preparation of Protonated-NHCs and Related Compounds*," J. Organometallic Chemistry, 2006, vol. 691, No. 14, pp. 3201-3205.

Kingsbury et al., "*A Recyclable Ru-based Metathesis Catalyst*," Journal of American Chemical Society, 1999, vol. 121, No. 4, pp. 791-799.

Lavallo et al., "*Stable Cyclic (Alkyl)(Amino)carbenes as Rigid or Flexible, Bulky Electron-Rich Ligands for Transition Metal Catalysts: A Quaternary Carbon Atom Makes the Difference*," Angew. Chem. Int. Ed., 2005, vol. 44, No. 35, pp. 5705-5709.

Lavallo et al., "*A Rigid Cyclic (Alkyl)(Amino)carbene Ligand Leads to Isolation of Low-Coordinate Transition Metal Complexes*," Angew. Chem. Int. Ed., 2005, vol. 44, No. 44, pp. 7236-7239.

Wilheim et al., "*Reactivity of Ru(H)(H2)Cl(PCy3)2 with Propargyl and Vinyl Chlorides: New Methodology to Give Metathesis-Active Ruthenium Carbenes*," Organometallics, 1997, vol. 16, No. 18, pp. 3867-3869.

Bergens et al., *A Ruthenium-Dihydrogen Putative Intermediate in Ketone Hydrogenation*, Journal of American Chemical Society, 2005, vol. 127, No. 12, pp. 4152-4153.

Fogg et al., *Carbonyl-Amplified Catalyst Performance: Balancing Stability Against Activity for Five-Coordinate Ruthenium Hydride and Hydridocarbonyl Catalysts*, Organometallics, 2009, vol. 28, No. 2, pp. 441-447.

Stuer et al., *A Tertiary Phosphine that is too Bulky: Preparation of Catalytically Less Active Carbene and Vinylidene Ruthenium(II) Complexes*, Journal of Organometallic Chemistry, Elsevier-Sequoia S.A. Lausanne, Ch, 2002, vol. 541, No. 1-2, pp. 203-207.

Stuer et al., *A Tertiary Phosphine that is too Bulky: Preparation of Catalytically Less Active Carbene and Vinylidene Ruthenium(II) Complexes,* Journal of Organometallic Chemistry, Elsevier-Sequoia S.A. Lausanne, CH, 2002, vol. 641, No. 1-2, pp. 203-207.

* cited by examiner

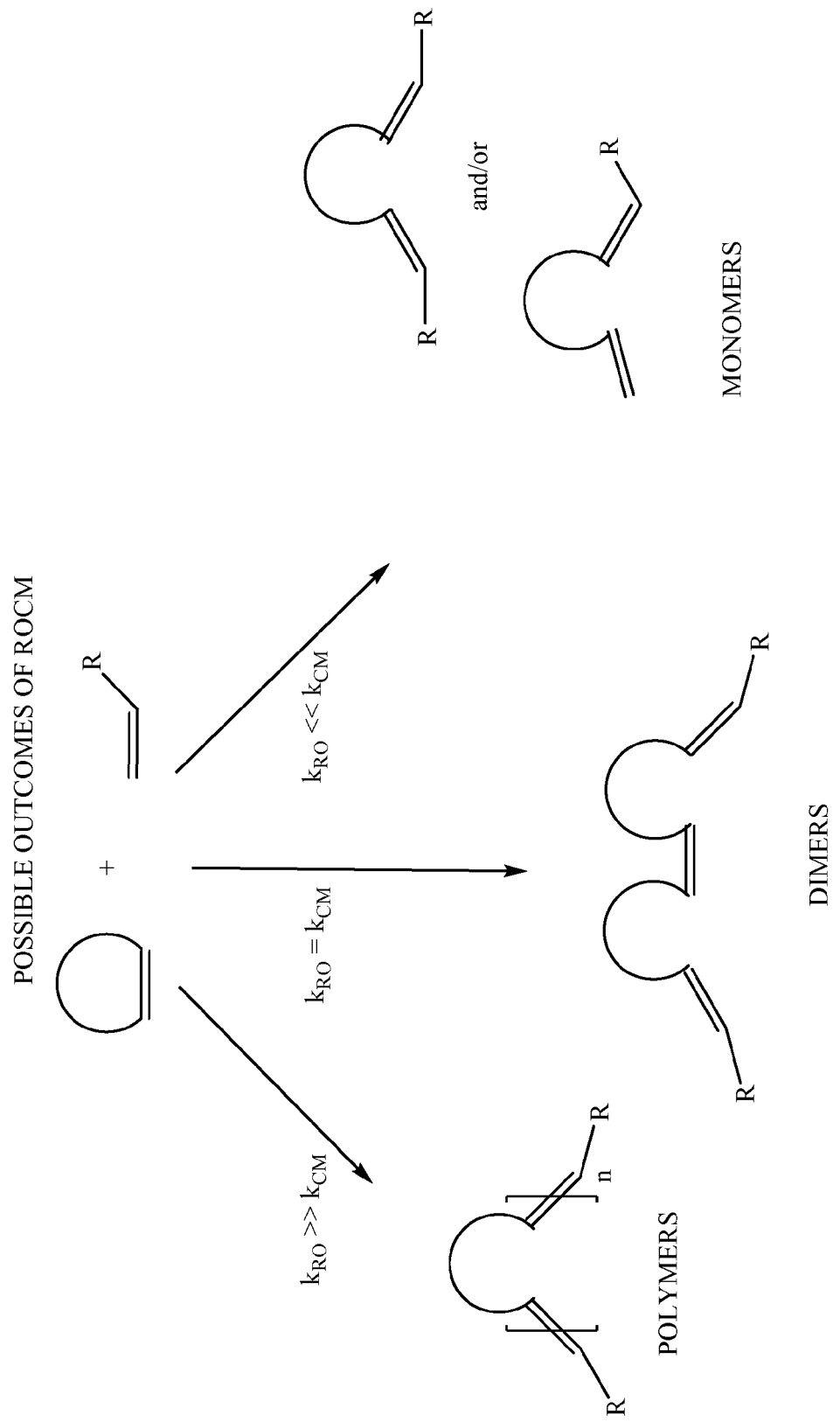

CLASS OF OLEFIN METATHESIS CATALYSTS, METHODS OF PREPARATION, AND PROCESSES FOR THE USE THEREOF

STATEMENT OF RELATED CASES

This application relates to U.S. Ser. No. 12/143,663, filed on Jun. 20, 2008; U.S. Ser. No. 12/487,739, filed on Jun. 19, 2009; U.S. Ser. No. 12/488,066, filed on Jun. 19, 2009; U.S. Ser. No. 12/488,093, filed on Jun. 19, 2009; U.S. Ser. No. 61/259,514, filed on Nov. 9, 2009; U.S. Ser. No. 61/259,521, filed on Nov. 9, 2009; U.S. Ser. No. 12/705,136, filed on Feb. 12, 2010; U.S. Ser. No. 61/314,388, filed on Mar. 16, 2010; U.S. Ser. No. 61/203,523, filed on Dec. 23, 2008; U.S. Ser. No. 12/660,815, filed on Mar. 4, 2010; U.S. Ser. No. 61/025,076, filed on Jan. 31, 2008; and U.S. Ser. No. 61/376,925 filed on Aug. 25, 2010.

FIELD OF THE INVENTION

This invention relates to a novel class of olefin metathesis catalysts, methods of preparation, and to processes using the olefin metathesis catalysts.

BACKGROUND OF THE INVENTION

In organic synthesis, a metathesis reaction is a catalytic reaction in which recombination of the double bonds occurs between two kinds of olefins or alkynes. The diversity of possible applications has led to the use of metathesis, particularly olefin metathesis, as a standard synthetic tool. Olefin metathesis applications include cross-metathesis (CM), ring-opening metathesis polymerization (ROMP), ring-opening cross metathesis (ROCM), ring-closing metathesis (RCM), and acyclic diene metathesis (ADMET). CM involves a carbon-carbon bond breaking/bond making process in which there is an overall exchange of double bond moieties between two olefins. ROMP involves the formation of polyolefins from the ring opening of cyclic olefins; ROCM involves a tandem sequence in which a cyclic olefin is opened and a second acyclic olefin is then cross metathesized onto the newly formed olefin termini; RCM involves the intramolecular transformation of an alpha, omega-diene to a cyclic olefin; and ADMET involves the polymerization of terminal dienes to polyenes. These synthetic tools have been applied to solve a wide range of synthetic problems, for example, RCM has been often featured as a key step in many synthetic solutions ranging from the total synthesis of natural products to the synthesis of catenanes. Also, industrially important polymers produced from ROMP include trans-polyoctenamer (polymer of cyclooctene, commercially available as Vestenamer® from Evonik Industries), polynorbornene (commercially available as Norsorex®); and polydicyclopentadiene (commercially available as Telene®, Metton®, and Pentam®). Another commercially significant application is ethenolysis, which is the CM of ethylene and internal olefins to produce alpha-olefins. Metathesis reactions are therefore indispensable as a synthetic tool for the formation of new carbon-carbon bonds.

Olefin metathesis may be catalyzed by one or more catalytic metals, usually one or more transition metals, such as the molybdenum-containing Schrock catalyst and the ruthenium- or osmium-containing Grubbs catalysts. Well-defined single component ruthenium or osmium catalysts have been previously described by, for example, U.S. Pat. Nos. 5,312,940; 5,342,909; 5,728,917; 5,710,298; 5,750,815; 5,831,108; 7,329,758; and PCT Publications WO 97/20865 and WO 97/29135, which are all incorporated herein by reference. These catalysts possess several advantageous properties, such as tolerance to a variety of functional groups and higher activity than previously known metathesis catalysts.

The ethenolysis of an internal olefin to produce linear alpha-olefins (LAOS) is of particular commercial significance. LAOs are useful as monomers or comonomers to produce polyalphaolefins (PAOs) and/or as intermediates in the production of epoxides, amines, oxo alcohols, synthetic lubricants, synthetic fatty acids, and alkylated aromatics. LAOs of industrial importance include 1-butene, 1-hexene, 1-octene, 1-decene, 1-undecene, 1-dodecene, and 1-tetradecene. However, the production of LAOs is often undesirably inefficient, creates unwanted by-products and wastes reactants and energy. Also, the major source of the starting materials for these commercial routes to LAOs are nonrenewable feedstreams including petroleum, coal, and natural gas.

Recently there has been a strong incentive to produce fuels and chemical products from renewable feedstreams, such as natural oils. For example, the development of biodiesel fuels is of great interest and some biodiesel-based materials are already commercially produced. Specifically, bio-diesel fuels made from plant oils are already on the market and demand for such fuels is expected to increase significantly over the next decade. LAOs may be produced from such renewable feedstreams by a CM reaction of the renewable feedstream, such as methyl oleate, with an olefin, such as ethylene, in the presence of a metathesis catalyst.

CM catalysts, reported thus far, for the ethenolysis of methyl oleate are typically ruthenium-based catalysts bearing phosphine or carbene ligands, such as those reported in Organometallics 2004, Vol. 23, No. 9, pp. 2027-2047 and WO 2008/010961. However, these catalysts were reported to be too expensive for industrial consideration due to high costs associated with the catalysts being derived from a low yielding synthesis (See Final Technical Report entitled "Platform Chemicals from an Oilseed Biorefinery," grant number DE-FG36-04GO14016, awarded by the Department of Energy). Furthermore, these ruthenium alkylidene catalysts are usually prepared by the reaction of ruthenium species with diazo compounds (J. Am. Chem. Soc. 1999, Vol. 121, No. 4, pp. 791-799). Therefore, cost and safety concerns associated with industrial scale reactions comprising diazo compounds have led to increased efforts to prepare ruthenium alkylidenes via alternate synthetic routes, such as using propargyl and vinyl chlorides (Organometallics, 1997, Vol. 16, No. 18, pp. 3867-3869). In order to obtain a commercially viable metathesis-based process, for example, LAO production via the CM of ethylene and biodiesel or natural oils, higher activity metathesis catalysts must be discovered.

There remains a need for catalysts which demonstrate high activity and selectivity in metathesis transformations which are capable of being synthesized by mild, affordable, and simple synthetic routes. The new catalysts disclosed herein are useful for metathesis transformations such as ROMP, CM, ROCM, and other metathesis transformations. The inventors have surprisingly found that a metathesis catalyst composition comprising a Group 8 metal hydride-dihydrogen complex and a ligand exchange agent and, optionally, an acetylene generates an active metathesis catalyst. The metathesis catalyst compositions of the present invention provide mild, affordable, and simple synthetic routes to desirable olefins and polyolefins, for example, LAOS, which in turn may be useful in the preparation of PAOs; poly(cyclic olefins); and other industrially relevant chemicals.

SUMMARY OF THE INVENTION

This invention relates to a metathesis catalyst composition comprising: (i) a Group 8 metal hydride-dihydrogen complex represented by the formula:

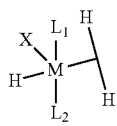

wherein M is a Group 8 metal; X is an anionic ligand; and $L_1$ and $L_2$ are neutral donor ligands; and (ii) a ligand exchange agent represented by the formula J-Y, wherein J is selected from the group consisting of hydrogen, a $C_1$ to $C_{30}$ hydrocarbyl, and a $C_1$ to $C_{30}$ substituted hydrocarbyl; and Y is selected from the group consisting of halides, alkoxides, aryloxides, and alkyl sulfonates.

This invention also relates to a method for making a metathesis catalyst comprising contacting a Group 8 metal hydride-dihydrogen complex with a ligand exchange agent; wherein the Group 8 metal hydride-dihydrogen complex is represented by the formula:

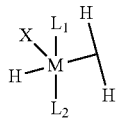

wherein M is a Group 8 metal; X is an anionic ligand; and $L_1$ and $L_2$ are neutral donor ligands; and wherein the ligand exchange agent is represented by the formula J-Y, wherein J is selected from the group consisting of hydrogen, a $C_1$ to $C_{30}$ hydrocarbyl, and a $C_1$ to $C_{30}$ substituted hydrocarbyl; and Y is selected from the group consisting of halides, alkoxides, aryloxides, and alkyl sulfonates.

This invention further relates to a process for performing a metathesis reaction comprising contacting at least one olefin with a metathesis catalyst, wherein the metathesis catalyst comprises a Group 8 metal hydride-dihydrogen complex represented by the formula:

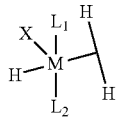

wherein M is a Group 8 metal; X is an anionic ligand; and $L_1$ and $L_2$ are neutral donor ligands.

BRIEF DESCRIPTION OF THE FIGURES

FIG. 1 is a representation of some of the possible outcomes of ring opening cross metathesis.

DETAILED DESCRIPTION

For the purposes of this invention and the claims thereto, the new numbering scheme for the Periodic Table Groups is used as in CHEMICAL AND ENGINEERING NEWS, 63(5), 27 (1985).

For the purposes of this invention and claims thereto, a "Group 8 metal" is an element from Group 8 of the Periodic Table.

For the purposes of this invention and the claims thereto, a "substituted hydrocarbyl" is a radical made of carbon and hydrogen where at least one hydrogen is replaced by a heteroatom.

For purposes of this invention and claims thereto, "alkoxides" include those where the alkyl group is a $C_1$ to $C_{10}$ hydrocarbyl. The alkyl group may be straight chain, branched, or cyclic. The alkyl group may be saturated or unsaturated. In some embodiments, the alkyl group may comprise at least one aromatic group. Preferred alkoxides include a $C_1$ to $C_{10}$ alkyl group, preferably methyl, ethyl, propyl, butyl, or isopropyl. Preferred alkoxides include those where the alkyl group is a phenol, substituted phenol (where the phenol may be substituted with up to 1, 2, 3, 4, or 5 $C_1$ to $C_{12}$ hydrocarbyl groups) or a $C_1$ to $C_{10}$ hydrocarbyl, preferably a $C_1$ to $C_{10}$ alkyl group, preferably methyl, ethyl, propyl, butyl, or phenyl.

For the purposes of this invention and the claims thereto, when a polymer is referred to as "comprising an olefin," the olefin present in the polymer is the polymerized form of the olefin. A "polymer" has one or more of the same or different mer units. A "copolymer" is a polymer having two or more mer units that are different from each other. An "oligomer" is a polymer having two to 100 mer units, where the mer units may be the same or different. Exemplary oligomers include dimers (two mer units), trimers (three mer units), tetramers (four mer units), decamers (ten mer units), and so on.

An "olefin," alternatively referred to as "alkene," is a linear, branched, or cyclic compound of carbon and hydrogen having at least one double bond. An "alpha-olefin" is an olefin having a double bond at the alpha (or 1-) position. A "linear alpha-olefin" or "LAO" is an olefin with a double bond at the alpha position and a linear hydrocarbon chain. A "polyalphaolefin" or "PAO" is a polymer having at least 100 mer units.

An "anionic ligand" is a negatively charged ligand which donates one or more pairs of electrons to a metal ion. A "neutral donor ligand" is a neutrally charged ligand which donates one or more pairs of electrons to a metal ion.

For the purposes of this invention and the claims thereto, when catalyst compositions are described as comprising neutral stable forms of the components, it is well understood by one of ordinary skill in the art, that the ionic form of the component is the form that reacts with the monomers to produce polymers. In the description herein, the transition metal compound used for catalysis may be described as a catalyst precursor, a pre-catalyst compound, a catalyst, or a catalyst compound, and these terms are used interchangeably. Additionally, a "reactor" is any container(s) in which a chemical reaction Occurs.

In recent years, the use of Group 8 metal complexes as catalysts in olefin polymerization processes (RCM, ROMP, ROCM) and olefin metathesis processes (CM, ADMET) has increased, mainly due to their remarkable stability towards diverse functional groups and protic solvents, and their ease of handling. However, existing methods of synthesis of Group 8 metal complexes remain inefficient and undesirable due to the multistep synthesis and associated purification steps; and the instability of some precursors (such as diphenylcyclopropene).

The present invention comprises novel catalyst compositions useful for the metathesis of olefins, methods of making such catalyst compositions, and processes for the use thereof. More particularly, the present invention comprises novel metathesis catalyst compositions which comprise the reaction product of: (i) a Group 8 metal hydride-dihydrogen complex; and (ii) a ligand exchange agent; methods of making such catalyst compositions and processes for the use thereof. In particular, the present invention comprises novel metathesis catalyst compositions useful to produce a linear alpha-olefin by a process comprising contacting at least one renewable feedstream with at least one lower olefin in the presence of the metathesis catalyst compositions of the present invention. In another embodiment, the present invention comprises novel metathesis catalyst compositions useful to produce a polyolefin by a process comprising contacting at least one cyclic olefin with the metathesis catalyst compositions of the present invention.

The inventors have discovered a new class of Group 8 metal catalyst compositions useful for metathesis reactions and an efficient and commercially economic route to these desirable Group 8 metal catalyst compositions, described herein. The inventors have further demonstrated utility of this class of Group 8 metal catalyst compositions for metathesis reactions, in particular, CM, ROCM, and ROMP. Advantageously, the new class of Group 8 metal catalyst compositions may be made in a single step and used in situ, thereby avoiding multistep synthesis and associated post-synthetic purification steps which tend to be costly, in terms of time, effort, and money.

Metathesis Catalyst Compositions

This invention relates to a metathesis catalyst composition comprising: (i) a Group 8 metal hydride-dihydrogen complex represented by the formula:

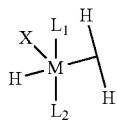

wherein:

M is a Group 8 metal, preferably ruthenium or osmium, preferably ruthenium;

X is an anionic ligand, preferably X is selected from the group consisting of halides, alkoxides, aryloxides, and alkyl sulfonates; preferably X is a halide; preferably X is a chloride; and $L_1$ and $L_2$ are neutral donor ligands, preferably $L_1$ and $L_2$ are independently selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof; preferably a phosphine, a sulfonated phosphine, an N-heterocyclic carbene, a cyclic alkyl amino carbene, and substituted analogs thereof; and (ii) a ligand exchange agent represented by the formula J-Y, wherein:

J is selected from the group consisting of hydrogen, a $C_1$ to $C_{30}$ hydrocarbyl, and a $C_1$ to $C_{30}$ substituted hydrocarbyl; and Y is an anionic group selected from the group consisting of halides, alkoxides, aryloxides, and alkyl sulfonates.

In all embodiments herein, "phosphines" may be represented by the formula $PR_3$, wherein R is independently selected from the group comprising hydrogen, $C_1$ to $C_{12}$ hydrocarbyl groups, substituted $C_1$ to $C_{12}$ hydrocarbyl groups, and halides; preferably methyl, ethyl, propyl, isopropyl, butyl, tert-butyl, pentyl, cyclopentyl, hexyl, cyclohexyl, heptyl, and substituted analogs and isomers thereof, preferably cyclohexyl.

For purposes of this invention and claims thereto, a "cyclic carbene" may be defined as a cyclic compound with a neutral dicoordinate carbon center featuring a lone pair of electrons. Such cyclic carbenes may be represented by the formula II below:

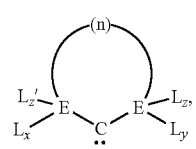

II where:

n is a linking group comprising from one to four ring vertices selected from the group consisting of C, Si, N, P, O, and S, with available valences optionally occupied by H, oxo, hydrocarbyl, or substituted hydrocarbyl groups; preferably, n comprises two ring vertices of carbon with available valences occupied by H, oxo, hydrocarbyl or substituted hydrocarbyl groups; preferably n is $C_2H_2$, $C_2H_4$, or substituted versions thereof;

E is independently selected from the group comprising C, N, S, O, and P, with available valences optionally occupied by Lx, Ly, Lz, and Lz'; preferably, at least one E is a C; preferably, one E is a C and the other E is a N; preferably, both E's are C; and Lx, Ly, Lz, and Lz' are independently selected from the group comprising hydrogen, hydrocarbyl groups, and substituted hydrocarbyl groups; preferably, Lx, Ly, Lz, and Lz' are independently selected from the group comprising a hydrocarbyl group and substituted hydrocarbyl group having 1 to 40 carbon atoms; preferably, Lx, Ly, Lz, and Lz' are independently selected from the group comprising $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, aryl, and substituted aryl; preferably, Lx, Ly, Lz, and Lz' are independently selected from the group comprising methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, toluoyl, chlorophenyl, 2,6-diethylphenyl, 2,6-diisopropylphenyl, 2-isopropylphenyl, 2-ethyl-6-methylphenyl, 3,5-ditertbutylphenyl, 2-tertbutylphenyl, and 2,3,4,5,6-pentamethylphenyl. Useful substituents include $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl, fluoro, chloro, bromo, iodo, oxo, amino, imine, nitrogen heterocycle, hydroxy, thiol, thiono, phosphorous, and carbene groups.

Examples of cyclic carbenes useful in embodiments of the present invention include:

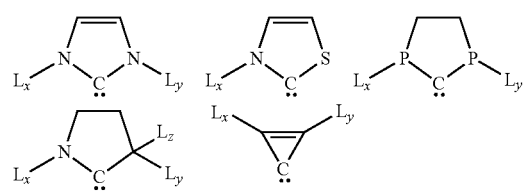

where Lx, Ly, and Lz are as defined above. In some embodiments, at least two of Lx, Ly, Lz, and Lz' may be joined to form a 3- to 12-membered spirocyclic ring, with available valences optionally occupied by H, oxo, halogens, hydrocarbyl or substituted hydrocarbyl groups. Useful substituents include $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl, fluoro, chloro, bromo, iodo, oxo, amino, imine, nitrogen heterocycle, hydroxy, thiol, thiono, phosphorous, and carbene groups.

Preferred cyclic carbenes include N-heterocyclic carbenes (NHCs). For purposes of this invention and claims thereto, NHCs are cyclic carbenes of the types described in Formula II above, where each E is N and the available valences on the N are occupied by Lx and Ly. NHCs may be represented by the formula:

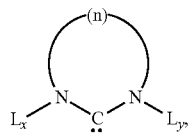

where:
n, Lx, and Ly are as described above.
Some particularly useful NHCs include:

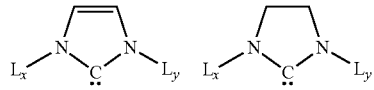

where Lx and Ly are as described above. Other useful NHCs include the compounds described in Hermann, W. A. Chem. Eur. J. 1996, 2, 772 and 1627; Enders, D. et al., Angew. Chem. Int. Ed. 1995, 34, 1021; Alder R. W., Angew. Chem. Int. Ed. 1996, 35, 1121; and Bertrand, G. et al., Chem. Rev. 2000, 100, 39.

Particularly preferred cyclic carbenes include cyclic alkyl amino carbines (CAACs). In all embodiments herein, CAACs are cyclic carbenes of the types described in Formula II above, where one E is N and the other E is C, and the available valences on the N and C are occupied by Lx, Ly, and Lz. CAACs may be represented by the formula:

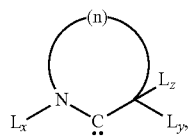

where:
n, Lx, Ly, and Lz are as described above.
Some particularly useful CAACs include:

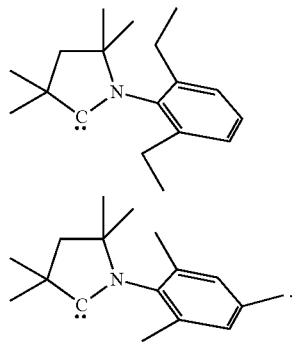

Other useful CAACs include the compounds described in U.S. Pat. No. 7,312,331 and Bertrand et al, *Angew. Chem. Int. Ed.* 2005, 44, 7236-7239.

Other carbenes useful in embodiments of the present invention include thiazolyldenes, P-heterocyclic carbenes (PHCs), and cyclopropenylidenes.

With respect to Group 8 metal hydride-dihydrogen complexes, $L_1$ and $L_2$ may be the same or different. For example, in some embodiments, such as bis-(tricyclohexylphosphine)(dihydrogen)rutheniumhydridochloride (also represented as $(Cy_3P)_2Ru(H_2)HCl$, where Cy is a cyclohexyl group), $L_1$ and $L_2$ are both cyclohexylphosphine groups $(Cy_3P)$. In other embodiments, such as $(OEt)(Cy_3P)Ru(H_2)HCl$ (where Et is ethyl), $L_1$ and $L_2$ are different, that is $L_1$ is an ethoxy group and $L_2$ is a cyclohexylphosphine group. In particular embodiments, at least one of $L_1$ and $L_2$ is selected from a phosphine, an N-heterocyclic carbene, a cyclic alkyl amino carbene, and substituted analogs thereof.

Some particularly useful Group 8 metal hydride-dihydrogen complexes include: (1,3-bis-(2,4,6-trimethylphenyl)-2-(imidazolidinylidene)(tricyclohexylphosphine)(dihydrogen) rutheniumhydridochloride, bis-(tricyclohexylphosphine)(dihydrogen)rutheniumhydridochloride, (1-mesityl-3-methyl-2H-4,5-dihydroimidazol-2-ylidene)(tricyclohexylphosphine)-(dihydrogen) rutheniumhydridochloride, 2-(2,6-diethylphenyl)-3,3,5,5-tetramethylpyrrolidine-(tricyclo hexylphosphine)-(dihydrogen)rutheniumhydridochloride.

In any embodiment herein, a "ligand exchange agent" is a compound represented by the formula J-Y, where J is selected from the group consisting of hydrogen, a $C_1$ to $C_{30}$ hydrocarbyl, and a $C_1$ to $C_{30}$ substituted hydrocarbyl, preferably a $C_2$ to $C_{15}$ hydrocarbyl or a $C_2$ to $C_{15}$ substituted hydrocarbyl, preferably a $C_2$ to $C_8$ hydrocarbyl or a $C_2$ to $C_8$ substituted hydrocarbyl, preferably ethyl, chloroethyl, dichloroethyl, trichloroethyl, tetrachloroethyl, pentachloroethyl; and Y is an anionic group selected from the group consisting of halides, alkoxides, aryloxides, and alkyl sulfonates, preferably a halide or an alkoxide, preferably a chloride.

Without wishing to be bound by theory, it is believed that ligand exchange agents react with the Group 8 metal hydride-dihydrogen complex described above, by abstracting a ligand ($L_1$ or $L_2$) and donating the heteroatom-containing group Y to the Group 8 metal hydride-dihydrogen complex. For example, where the Group 8 metal hydride-dihydrogen complex is $(Cy_3P)_2Ru(H_2)HCl$ and the ligand exchange agent is hexachloroethane (Y is a chloride group), the hexachloroethane is thought to abstract a phosphine ligand $(Cy_3P)$ and donate a chloride heteroatom to the Group 8 metal hydride-dihydrogen complex. Hexachloroethane has been reported to act as a mild chlorinating agent for tungsten complexes in Organometallics 1984, 3, 476-484. Here, the inventors demonstrate the utility of ligand exchange agents, such as hexachloroethane, for generating active Group 8 metal complexes by both abstracting a ligand and donating a heteroatom-containing group to the Group 8 metal complex. Useful ligand exchange agents include halogenating agents wherein Y is a halide, preferably chlorinating agents. wherein Y is a chloride, preferably tetrachloroethane, pentachloroethane, hexachloroethane, preferably pentachloroethane or hexachloroethane.

In particular embodiments, the metathesis catalyst composition further comprises an acetylene compound represented by the formula:

wherein $R_1$ and $R_2$ are independently selected from the group consisting of hydrogen, a $C_1$ to $C_{30}$ hydrocarbyl, and a $C_1$ to $C_{30}$ substituted hydrocarbyl; preferably from the group consisting of a hydrogen, a $C_2$ to $C_{15}$ hydrocarbyl, and a $C_2$ to $C_{15}$ substituted hydrocarbyl; preferably from the group consisting of a hydrogen, a $C_2$ to $C_6$ hydrocarbyl, and a $C_2$ to $C_6$ substituted hydrocarbyl; preferably at least one of $R_1$ and $R_2$ is hydrogen; preferably at least one of $R_1$ and $R_2$ is ethyl, propyl, butyl, phenyl, hexyl, cyclohexyl. Useful acetylene compounds include: acetylene, methylacetylene, ethylacetylene, propylacetylene, butylacetylene, pentylacetylene, hexylacetylene, phenylacetylene, isomers, and substituted analogs thereof, preferably acetylene or phenylacetylene.

Exemplary catalyst compositions, described herein, include a composition of a Group 8 metal hydride-dihydrogen complex and a ligand exchange agent; and a composition of a Group 8 metal hydride-dihydrogen complex, a ligand exchange agent, and an acetylene, more particularly, a composition of a Group 8 metal hydride-dihydrogen complex and hexachloroethane; and a composition of a Group 8 metal hydride-dihydrogen complex, hexachloroethane, and an acetylene, even more particularly, a composition of RuClH$(H_2)(PCy_3)_2$ and pentachloroethane; and a composition of RuClH$(H_2)(PCy_3)_2$, hexachloroethane, and phenylacetylene.

In certain embodiments, the catalyst composition employed in the process of this invention may be bound to or deposited on a solid support. In particular, the Group 8 metal hydride-dihydrogen complex may be bound to or deposited onto a solid support, which may simplify catalyst recovery. In addition, the support may increase catalyst strength and attrition resistance. Suitable catalyst supports include, without limitation, silicas, aluminas, silica-aluminas, aluminosilicates, including zeolites, and other crystalline porous aluminosilicates; as well as titanias, zirconia, magnesium oxide, carbon, and cross-linked polymeric resins, such as functionalized cross-linked polystyrenes, e.g., chloromethyl-functionalized cross-linked polystyrenes; preferably silica or alumina. The Group 8 metal hydride-dihydrogen complex may be deposited onto the support by any method known to those skilled in the art, including, for example, impregnation, ion-exchange, deposition-precipitation, and vapor deposition. Alternatively, a component of the catalyst composition, such as the Group 8 metal hydride-dihydrogen complex, may be chemically bound to the support via one or more covalent chemical bonds, for example, the catalyst composition may be immobilized by one or more covalent bonds with one or more of substituents of a ligand of the Group 8 metal hydride-dihydrogen complex. For example, the Group 8 metal hydride-dihydrogen complex may be deposited onto a silica support. Further, the Group 8 metal hydride-dihydrogen complex may be preloaded onto the solid support before forming the catalyst composition of the present invention. Alternatively, the supported catalyst composition may be generated in situ.

If a catalyst support is used, the catalyst compound may be loaded onto the catalyst support in any amount, provided that the metathesis process of this invention proceeds to the metathesis products. Generally, the catalyst compound is loaded onto the support in an amount based on the weight of the transition metal, preferably the Group 8 metal, preferably ruthenium or osmium, relative to the total weight of the catalysts plus support. The catalyst compound may be loaded onto the support in an amount greater than about 0.01 weight percent of the Group 8 metal, and preferably, greater than about 0.05 weight percent of the Group 8 metal. Generally, the catalyst compound is loaded onto the support in an amount that is less than about 20 weight percent of the Group 8 metal, and preferably, less than about 10 weight percent of the Group 8 metal.

Synthesis of Metathesis Catalysts

The metathesis catalysts described herein may be synthesized by any methods known to those skilled in the art. In general, the metathesis catalysts of the present invention are made by contacting a Group 8 metal hydride-dihydrogen complex of the formula

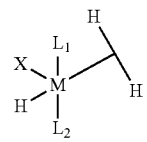

with a ligand exchange agent of the formula J-Y, where both the Group 8 metal hydride-dihydrogen complex and the ligand exchange agent are as described above, and whereby the ligand exchange agent is believed to both abstract a ligand from the Group 8 metal hydride-dihydrogen complex and donate the heteroatom Y to the Group 8 metal hydride-dihydrogen complex. The Group 8 metal hydride-dihydrogen complex and the ligand exchange agent may be made by any suitable method.

In particular embodiments, the metathesis catalysts of the present invention are made by contacting a Group 8 metal hydride-dihydrogen complex of the formula

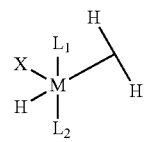

with a ligand exchange agent of the formula J-Y, and an acetylene of the formula

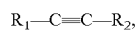

$R_1$—C≡C—$R_2$, where each of the Group 8 metal hydride-dihydrogen complex, the ligand exchange agent, and the acetylene are as described above, and whereby the ligand exchange agent is believed to both abstract a ligand from the Group 8 metal hydride-dihydrogen complex and donate the heteroatom Y to the Group 8 metal hydride-dihydrogen complex.

The Group 8 metal hydride-dihydrogen complex, the ligand exchange agent, and the acetylene may be made by any suitable method. Representative methods of synthesizing the Group 8 metal hydride-dihydrogen complex of the type described herein include, for example, those reported in Organometallics 1997, 16, 3867.

In some embodiments, the metathesis catalysts of the present invention are made by contacting the Group 8 metal hydride-dihydrogen complex with a ligand exchange agent, and, optionally, an acetylene, as described above, where any of the reactants may be dissolved in a suitable solvent, include non-coordinating, inert liquids. Examples include straight and branched-chain hydrocarbons such as isobutane, butane, pentane, isopentane, hexanes, isohexane, heptane, octane, dodecane, and mixtures thereof; cyclic and alicyclic hydrocarbons such as cyclohexane, cycloheptane, methylcyclohexane, methylcycloheptane, and mixtures thereof, including those that can be found commercially (Isopar™); perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable diluents/solvents also include aromatic hydrocarbons, such as toluene or xylenes, and chlorinated solvents, such as dichloromethane. In other embodiments, the reactants may be used neat, that is, in the absence of a carrier solvent.

In some embodiments, the metathesis catalysts of the present invention are made by contacting the Group 8 metal hydride-dihydrogen complex with a ligand exchange agent, and, optionally, an acetylene, as described above, in any amount sufficient to form the metathesis products. In all embodiments herein, the "catalyst loading" is the number of moles of olefin relative to the number of moles of Group 8 metal hydride-dihydrogen complex. Preferably, the catalyst loading is typically greater than 10:1; preferably, greater than 100:1; preferably, greater than 1,000:1; preferably, greater than 10,000:1; preferably, greater than 25,000:1; preferably, greater than 50,000:1; preferably, greater than 100,000:1. Alternately, the molar ratio of renewable feedstream to metathesis catalyst is typically less than 10,000,000:1; preferably, less than 1,000,000:1; and more preferably, less than 500,000:1.

In a preferred embodiment, from 0.005 nmoles to 500 nmoles; preferably, from 0.1 to 250 nmoles; and most preferably, from 1 to 50 nmoles of the metathesis catalyst are charged to the reactor per 3 mmoles of olefin.

In some embodiments, the ligand exchange agent, and, optionally, an acetylene may be used in equimolar amounts, relative to the amount of olefin used. In other embodiments, an excess of the ligand-exchange agent, and, optionally, an acetylene may be used, relative to the amount of olefin used, for example, the ligand-exchange agent and, optionally, the acetylene may be used in amounts of 5 molar equivalents, 10 molar equivalents, 15 molar equivalents, 50 molar equivalents, 100 molar equivalents; preferably 10 molar equivalents, 50 molar equivalents. In some embodiments, the catalyst loading is less than 100,000:1 and the ligand exchange agent, and, optionally, an acetylene are used in equimolar amounts, relative to the amount of olefin used. In other embodiments, the catalyst loading is less than 100,000:1 and the ligand exchange agent, and, optionally, an acetylene are used in a 10 molar equivalent amount, relative to the amount of olefin used in the reaction.

In some embodiments, the contacting process may occur in the presence of heat, for example, heat to reflux, for a time period appropriate to yield the desired metathesis catalyst. The ligand exchange reaction may occur faster in such embodiments. The contacting process may occur at a temperature of 20 to 300° C. (preferably, 20 to 200° C.; preferably, 25 to 100° C.; preferably, 25 to 60° C.) for a contacting time of 0.5 seconds to 48 hours (preferably, 0.25 to 24 hours; preferably, 30 minutes to 2 hours).

Without wishing to be bound by theory, the inventors believe that the active metathesis catalysts are generated due to the ligand exchange agent, for example, hexachloroethane, serving two functions, specifically, to remove a ligand, for example, a phosphine, from the Group 8 metal hydride-dihydrogen complex and to donate a heteroatom, for example, a chloride, to the Group 8 metal hydride-dihydrogen complex. Generally, the active metathesis catalyst may be generated through reaction with olefin reactant or, in embodiments where an acetylene is part of the catalyst composition, by rapid insertion of an acetylene into the Group 8 metal hydride, as shown below:

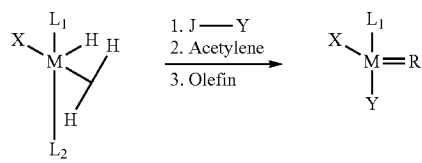

where $L_1$, $L_2$, M, X, J, and Y are as defined above and R is a hydrocarbyl group derived from the acetylene or the olefin, and is also described as above.

The inventors conducted NMR experiments to investigate the behavior of the ligand exchange agents pentachloroethane and hexachloroethane. Contacting the free phosphine ligand tricyclohexylphosphine ($Cy_3P$) with hexachloroethane generated the species $Cy_3PCl_2$ ($^{31}P$ NMR($CH_2Cl_2$): δ 107.4). Similarly, contacting the free phosphine ligand tricyclohexylphosphine ($Cy_3P$) with pentachloroethane generated the species $Cy_3PCl_2$ ($^{31}P$ NMR($CH_2Cl_2$): δ 107.3). A Group 8 metal hydride-dihydrogen complex of the formula $(Cy_3P)_2RuH(H_2)Cl$ was found to be stable in deuterated dichloromethane ($^{31}P$ NMR ($CH_2Cl_2$): δ 53.8). However, on contacting the $(Cy_3P)_2RuH(H_2)Cl$ with the ligand exchange agent hexachloroethane, a reaction occurred, producing $Cy_3PCl_2$ ($^{31}P$ NMR($CH_2Cl_2$): δ 117.4, 107.9 ($Cy_3PCl_2$), and 92.3 (br)). The inventors suggest that the reaction indicates that hexachloroethane abstracts a phosphine ligand from $(Cy_3P)_2Ru(H_2)HCl$ through an oxidation pathway and donates a chloride heteroatom to the ruthenium complex, producing $Cy_3PCl_2$ as a byproduct. Further, during a ROMP reaction, such as described herein, on contacting the $(Cy_3P)_2RuH(H_2)Cl$ with the ligand exchange agent hexachloroethane and the olefin dicyclopentadiene, a reaction occurred, producing $Cy_3PCl_2$ and poly(dicyclopentadiene) ($^{31}P$ NMR($CH_2Cl_2$): δ 118 and 109 ($Cy_3PCl_2$)). The inventors surmise that hexachloroethane abstracts a phosphine ligand from $(Cy_3P)_2Ru(H_2)HCl$ through an oxidation pathway and donates a chloride heteroatom to the ruthenium complex. The active metathesis catalyst is probably generated through insertion into the dicyclopentadiene (DCPD) double bond, as shown below:

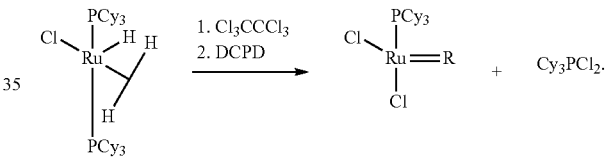

Accordingly, the inventors have surprisingly discovered that metathesis catalyst compositions comprising: (i) a Group 8 metal hydride-dihydrogen complex; and (ii) a ligand exchange agent, as previously described, generate an active catalyst suitable for metathesis reactions.

Metathesis Reactions

The catalysts of the present invention may be used for any metathesis reaction, including ROMP, RCM, CM, ROCM, and so on, by contacting the inventive catalysts with olefins. In some embodiments, a process for performing a metathesis reaction comprises contacting at least one olefin with a metathesis catalyst, wherein the metathesis catalyst comprises a Group 8 metal hydride-dihydrogen complex represented by the formula:

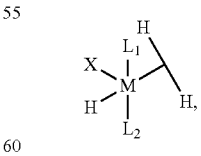

where M, X, $L_1$, and $L_2$ are as described above.

In other embodiments, a method for performing a metathesis reaction comprises contacting at least one olefin with a metathesis catalyst, wherein the metathesis catalyst comprises (i) a Group 8 metal hydride-dihydrogen complex represented by the formula:

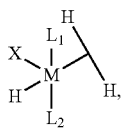

where M, X, $L_1$, and $L_2$ are as described above; and
(ii) a ligand exchange agent represented by the formula J-Y, where J is selected from the group consisting of hydrogen, a $C_1$ to $C_{30}$ hydrocarbyl, and a $C_1$ to $C_{30}$ substituted hydrocarbyl; and
Y is selected from the group consisting of halides, alkoxides, aryloxides, and alkyl sulfonates.

In yet other embodiments, a method for performing a metathesis reaction comprises contacting at least one olefin with a metathesis catalyst, wherein the metathesis catalyst comprises (i) a Group 8 metal hydride-dihydrogen complex represented by the formula:

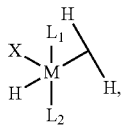

where M, X, $L_1$, and $L_2$ are as described above;
(ii) a ligand exchange agent represented by the formula J-Y, where J is selected from the group consisting of hydrogen, a $C_1$ to $C_{30}$ hydrocarbyl, and a $C_1$ to $C_{30}$ substituted hydrocarbyl; and Y is selected from the group consisting of halides, alkoxides, aryloxides, and alkyl sulfonates; and
(iii) an acetylene compound represented by the formula:

where $R_1$ and $R_2$ are independently selected from the group consisting of hydrogen, a $C_1$ to $C_{30}$ hydrocarbyl, and a $C_1$ to $C_{30}$ substituted hydrocarbyl.

In particular embodiments, a method for performing a metathesis reaction comprises contacting at least one olefin with a metathesis catalyst, wherein the metathesis catalyst comprises (i) a Group 8 metal hydride-dihydrogen complex as described above; (ii) hexachloroethane; and (iii) phenylacetylene.

The inventors have surprisingly discovered that at a particular catalyst loading for a ROMP reaction, the metathesis reaction proceeds slowly in the presence of the Group 8 metal hydride-dihydrogen complex, for example, in Example 6 the polymerization to a viscous poly(dicyclopentadiene) (poly-DCPD) takes three hours. At the same catalyst loading, the metathesis reaction proceeds at about the same rate in the presence of the Group 8 metal hydride-dihydrogen complex and the ligand exchange agent, for example, in Example 8 the polymerization to a viscous poly-DCPD also takes three hours. However, at the same catalyst loading, the metathesis reaction proceeds faster in the presence of the Group 8 metal hydride-dihydrogen complex, the ligand exchange agent, and acetylene, for example, in Examples 1 and 4 the polymerization to a viscous poly-DCPD takes just 6 minutes and four minutes, respectively.

Similarly, at a particular catalyst loading for a CM reaction, the CM reaction proceeds slowly in the presence of the Group 8 metal hydride-dihydrogen complex, for example, Example 18, with a conversion of 1-hexene to cis/trans-5-decene of 2.2%. At the same catalyst loading, the CM reaction proceeds at about the same rate in the presence of the Group 8 metal hydride-dihydrogen complex and the ligand exchange agent, for example, Example 20, with a conversion of 1-hexene to cis/trans-5-decene of 2.1%. However, at the same catalyst loading, the CM reaction proceeds even faster in the presence of the Group 8 metal hydride-dihydrogen complex, the ligand exchange agent, and acetylene, for example, Examples 16 and 17, with a conversion of 1-hexene to cis/trans-5-decene of 7.4% and 4.5%, respectively.

The inventors have further surprisingly discovered that the metathesis catalyst compositions of the present invention are also useful as isomerization catalysts. In some embodiments herein, the isomerization catalysts isomerizes an alpha olefin into its respective internal isomers. For example, the inventors found that 1-hexene was isomerized to internal isomers, such as hex-2-ene, hex-3-ene, and so on. In Example 16, 31.0% of the 1-hexene was converted to internal olefins, while 7.4% of the 1-hexene was converted to the cross-metathesis product of cis/trans-5-decene.

Any olefin may be used in the processes for performing a metathesis reaction of this invention. The olefin may have one carbon-carbon double bond, or alternatively, two or more carbon-carbon double bonds. Since the metathesis reaction can occur at any double bond, olefins having more than one double bond will produce more metathesis products. Accordingly, in some embodiments, it is preferred to employ an olefin having only one carbon-carbon double bond. The double bond may be, without limitation, a terminal double bond or an internal double bond. The olefin may also be substituted at any position along the carbon chain with one or more substituents. In some embodiments, the one or more substituents are essentially inert with respect to the metathesis process. Suitable substituents include, without limitation, alkyl, preferably, $C_{1-6}$ alkyl; cycloalkyl, preferably, $C_{3-6}$ cycloalkyl; as well as hydroxy, ether, keto, aldehyde, and halogen functionalities. The reactant olefin may be chosen, depending on the application the metathesis product may be employed in, as illustrated in the applications below. The reactant olefin may be at least one of an acyclic olefin, an alpha olefin, a renewable feedstream, a cyclic olefin, and an internal olefin.

Production of LAOs from Renewable Feedstreams by Cross Metathesis

In particular embodiments, the present invention involves a process for performing a metathesis reaction, as described above, wherein the at least one olefin comprises at least one lower olefin and at least one renewable feedstream. In such embodiments, the metathesis product comprises a linear alphaolefin (LAO).

Lower Olefins

For purposes of this invention and the claims thereto, the term "lower olefin" refers to an organic compound containing at least one carbon-carbon double bond and having 6 carbon atoms or less. Lower olefins are represented by the formula: R*—HC=CH—R*, wherein each R* is, independently, hydrogen or a $C_1$ to $C_2$ hydrocarbyl; preferably, hydrogen, methyl, or ethyl; more preferably, R* is hydrogen. In a preferred embodiment, both R* are the same; preferably, both R* are hydrogen. For example, ethylene is a lower olefin that is particularly useful in embodiments herein.

Non-limiting examples of suitable lower olefins include ethylene, propylene, butene, butadiene, and isomers thereof. Preferably, the lower olefin is ethylene.

Renewable Feedstreams

"Renewable feedstreams" as used herein, means starting materials that are derived from renewable sources. A source is considered renewable if it is replenished by natural means.

Renewable feedstreams useful herein include fatty acids, fatty acid esters, natural oils, biodiesel, triacylglycerides, or mixtures thereof.

Natural Oils

"Natural oils," as used herein, includes oils derived from biological sources, including animals, plants, algae, and fungi. Natural oils typically comprise mixtures of fatty acids and fatty acid esters, which are discussed below. These fatty acids often naturally occur as esters of three fatty acids and glycerol, known as triglycerides, also discussed below.

Natural oils useful herein preferably contain fatty acids and fatty acid esters with at least one site of unsaturation and include, but are not limited to, canola oil, corn oil, soybean oil, rapeseed oil, algae oil, peanut oil, mustard oil, sunflower oil, tung oil, tall oil, perilla oil, grapeseed oil, linseed oil, safflower oil, pumpkin oil, palm oil, Jatropha oil, high-oleic soybean oil, high-oleic safflower oil, high-oleic sunflower oil, mixtures of animal and vegetable fats and oils, beef tallow, castor bean oil, dehydrated castor bean oil, cucumber oil, poppyseed oil, flaxseed oil, lesquerella oil, walnut oil, cottonseed oil, meadowfoam, tuna oil, sesame oils, waste oils/greases, and mixtures thereof.

While readily available vegetable oils are preferred sources of fatty acids for practicing disclosed embodiments of the present process, fatty acids and fatty acid esters available from animal fats including, without limitation, lard, and fish oils, such as sardine oil, tuna oil, herring oil, and the like, may be employed in embodiments herein. Furthermore, particular fatty acids or fatty acid precursors may also be advantageously available from genetically modified organisms, such as genetically modified plants, particularly genetically modified algae. Such genetically modified organisms are typically designed to produce a desired fatty acid or fatty acid precursor biosynthetically or to advantageously produce increased amounts of such compounds. Preferred natural oils include palm oil, soybean oil, sunflower oil, canola oil, Jatropha oil, and algae oil.

Fatty Acids and Fatty Acid Esters

Fatty acids are carboxylic acids with saturated or unsaturated aliphatic tails that occur naturally in many different natural oils. Fatty acid esters are alkyl esters of fatty acids; preferably, $C_1$ to $C_{12}$ esters; preferably, $C_1$ to $C_5$ esters; preferably, methyl, ethyl, n-propyl, n-butyl esters; more preferably, methyl or ethyl esters. An unsaturated fatty acid comprises a long carbon chain containing at least one carbon-carbon double bond and terminating in a carboxylic acid group. An unsaturated fatty acid ester also comprises a long carbon chain containing at least one carbon-carbon double bond but terminates in a carboxylate group.

Unsaturated fatty acids, unsaturated fatty acid esters, and mixtures thereof are of particular importance in embodiments herein. Any unsaturated fatty acid or fatty acid ester may be suitably employed to produce LAOS, provided that the unsaturated fatty acid or fatty acid ester can be metathesized in the manner disclosed herein. At least one carbon-carbon double bond may occur at any internal location, usually about the middle of the aliphatic tail. A terminal carbon-carbon double bond, at the opposite end of the carbon chain relative to the carboxylic acid or carboxylate group, is also suitably employed, although terminal carbon-carbon double bonds occur less commonly in fatty acids.

Monounsaturated fatty acids and fatty acid esters contain one carbon-carbon double bond in the long aliphatic tail. Examples of monounsaturated fatty acids and fatty acid esters useful herein include myristoleic acid, palmitoleic acid, sapienic acid, oleic acid, erucic acid, and alkyl esters thereof. Polyunsaturated fatty acids and fatty acid esters contain two or more carbon-carbon double bonds in the long aliphatic tail. Examples of polyunsaturated fatty acids and esters useful herein include linoleic acid, linolenic acid, arachidonic acid, eicosapentaenoic acid, docosahexaenoic acid, and alkyl esters thereof. Some natural oils may contain fatty acids and fatty acid esters that are polyunsaturated, and some of the sites of unsaturation may be internal. For instance, oleic acid, linoleic acid, and linolenic acid, and their respective esters are examples of fatty acid and fatty acid esters with internal sites of unsaturation. Methyl oleate has one internal double bond, methyl linoleate has two internal double bonds, and methyl linolenoate has three internal double bonds, as shown below.

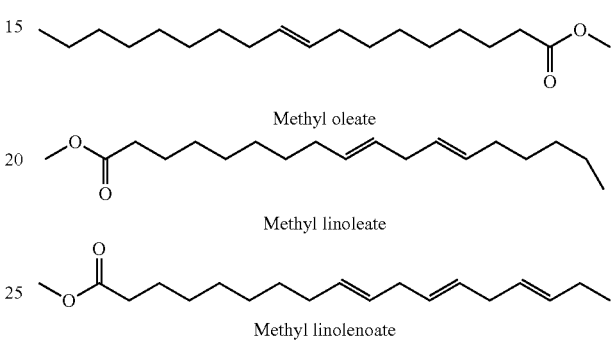

Fatty acids and fatty acid esters useful herein include monounsaturated fatty acids and esters thereof, polyunsaturated fatty acids and esters thereof, and mixtures of monounsaturated and polyunsaturated fatty acids and esters thereof.

Typically, the unsaturated fatty acid will contain greater than 8 carbon atoms; preferably, greater than 10 carbon atoms; and more preferably, greater than 12 carbon atoms. Typically, the unsaturated fatty acid will contain less than 50 carbon atoms; preferably, less than 35 carbon atoms; and more preferably, less than 25 carbon atoms.

The unsaturated fatty acid may be straight or branched, and may be substituted along the fatty acid chain with one or more substituents, provided that the one or more substituents are substantially inert with respect to the metathesis process. Non-limiting examples of suitable substituents include alkyl moieties, preferably, $C_{1-10}$ alkyl moieties, including, for example, methyl, ethyl, propyl, butyl, and the like; cycloalkyl moieties, preferably, $C_{4-8}$ cycloalkyl moieties, including for example, cyclobutyl, cyclopentyl, cyclohexyl and cyclooctyl; monocyclic aromatic moieties, preferably, $C_6$ aromatic moieties, including for example, phenyl; and alkylaryl moieties, preferably, $C_{7-16}$ alkylaryl moieties, including, for example, tolyl, ethylphenyl, xylyl, and the like; as well as hydroxyl, ether, keto, aldehyde, and halide, preferably, chloride and bromide, functionalities.

Non-limiting examples of suitable unsaturated fatty acid and fatty acid esters include 3-hexenoic (hydrosorbic), trans-2-heptenoic, 2-octenoic, 2-nonenoic, cis- and trans-4-decenoic, 9-decenoic (caproleic), 10-undecenoic (undecylenic), trans-3-dodecenoic (linderic), tridecenoic, cis-9-tetradeceonic (myristoleic), pentadecenoic, cis-9-hexadecenoic (cis-9-palmitoelic), trans-9-hexadecenoic (trans-9-palmitoleic), 9-heptadecenoic, cis-6-octadecenoic (petroselinic), trans-6-octadecenoic (petroselaidic), cis-9-octadecenoic (oleic), trans-9-octadecenoic (elaidic), cis-11-octadecenoic, trans-11-octadecenoic (vaccenic), cis-5-eicosenoic, cis-9-eicosenoic (gadoleic), cis-11-docosenoic (cetoleic), cis-13-docosenoic (erucic), trans-13-docosenoic (brassidic), cis-15-tetracosenoic (selacholeic), cis-17-hexacosenoic (ximenic), and cis-21-triacontenoic (lumequeic) acids, as well as 2,4-hexadienoic (sorbic), cis-9-cis-12-octadecadienoic (linoleic), cis-9-cis-12-cis-15-octadecatrienoic (linolenic), eleostearic, 12-hydroxy-cis-9-octadecenoic (ricinoleic), and like acids and corresponding esters thereof. Particularly preferred fatty acids and fatty acid esters useful herein include oleic acid, linoleic acid, linolenic acid, and esters thereof.

The natural oils useful in the processes described herein typically include a mixture of saturated (Cn:0), monounsaturated (Cn:1), and polyunsaturated (Cn:2, 3, etc.) fatty acids, where n is the number of carbon atoms present in the fatty acid. For example, the fatty acid profiles of several potential natural oil feedstreams are shown in Table 1, below.

TABLE 1

Fatty Acid Profile of Several Typical Natural Oils

| Fatty Acid | Wt % | | | | |
|---|---|---|---|---|---|
| | Palm | Soybean | Sunflower | Canola | Jatropha |
| Myrisitic (C14:0) | 1.1 | 0.1 | 0 | 0 | 0.1 |
| Palmitic (C16:0) | 44 | 11.0 | 0 | 3.9 | 14.2 |
| Stearic (C18:0) | 4.5 | 4.0 | 4.5 | 1.9 | 7 |
| Oleic (C18:1) | 39.2 | 23.4 | 21.1 | 64.1 | 44.7 |
| Linoleic (C18:2) | 10.1 | 53.2 | 66.2 | 18.7 | 32.8 |
| Linolenic (C18:3) | 0.4 | 7.8 | 0 | 9.2 | 0.2 |
| Arachidic (C20:0) | 0 | 0 | 0.3 | 0.6 | 0.2 |
| Miscellaneous | 0.7 | 0.5 | 7.9 | 1.6 | 0.8 |

In a preferred embodiment, the renewable feedstream comprises a combination of natural oils. Preferred combinations include two or more of tall oil, palm oil, tallow, waste grease, rapeseed oil, canola oil, soybean oil, sunflower oil, Jatropha oil, and algae oil. Alternate useful combinations include two (three or four) or more of soybean oil, sunflower oil, palm oil, canola oil, rapeseed oil, algae oil, Jatropha oil, and tallow.

Triacylglycerides (TAGs)

The chief constituent of natural oils is triacylglycerides (TAGs), also called triglycerides. TAGs are a naturally occurring ester of three fatty acids and glycerol. The three fatty acids can be all different, all the same, or only two the same. They can be saturated or unsaturated fatty acids, and the saturated fatty acids may have one or multiple sites of unsaturations. Chain lengths of the fatty acids in naturally occurring TAGs can be of varying lengths, but 16, 18, and 20 carbons are the most common. Natural fatty acids found in plants and animals are typically composed of even numbers of carbon atoms due to the way they are bio-synthesized. Most natural fats contain a complex mixture of individual triglycerides and because of this, they melt over a broad range of temperatures.

TAGs typically have the chemical structure:

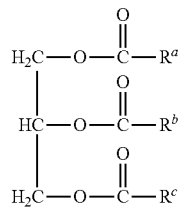

where $R^a$, $R^b$, and $R^c$ each, independently, represent a saturated or non-saturated hydrocarbon chain (preferably, $R^a$, $R^b$, and $R^c$ each, independently, are a $C_{12}$ to $C_{28}$ alkyl or olefin, preferably, $C_{16}$ to $C_{22}$ alkyl or olefin).

Different vegetable oils have different fatty acid profiles, with the same or different fatty acids occurring on a single glycerol. For example, an oil can have linoleic, oleic, and stearic acids attached to the same glycerol, with each of $R^a$, $R^b$, and $R^c$ representing one of these three fatty acids. In another example, there can be two oleic acids and one stearic acid attached to the same glycerol, each of $R^a$, $R^b$, and $R^c$ representing one of these fatty acids.

In one embodiment, a useful TAG consists of three unsaturated fatty acids, where at least one fatty acid is oleic acid. In another embodiment, a useful TAG consists of three unsaturated fatty acids, where at least one fatty acid is linoleic acid. In yet another embodiment, a useful TAG consists of three unsaturated fatty acids, where at least one fatty acid is oleic acid and at least one fatty acid is linoleic acid. In other embodiments, a mixture of different TAGs may be used.

Other materials containing fatty acid glycerides or other fatty acid esters can also be used, including phospholipids, lysophospholipids, and fatty acid wax esters. The free fatty acid content of useful natural oils is preferably about 0.1 wt % or less when employed in a basic homogeneous catalyst esterification reaction. Higher levels can be utilized as well, and levels up to about 3.0 wt %, or even as high as about 15.0 wt % or more may be tolerated.

TAGs may be processed by transesterification with alcohols to give biodiesel. Biodiesel is typically a mixture of mono-alkyl fatty acid esters, and is useful as a renewable feedstream for methods disclosed herein. The processing of natural oils is discussed in greater detail below.

Processing of Renewable Feedsteams

Raw or unrefined oils can be used in certain embodiments. However, filtered and refined oils are typically preferred. Use of degummed and filtered feedstreams minimizes the potential for emulsification and blockage in the reactor systems. Feedstreams with high water content can be dried before use. Feedstreams with high free fatty acid content can be passed through an esterification process to reduce the free fatty acid content before the process of esterification to convert fatty acid glycerides to monoalkyl esters. The reduction of free fatty acids and the conversion of fatty acid glycerides can be accomplished in the same processing step. Feedstreams containing other organic compounds (such as hexane, heptane, isohexane, etc.) can typically be processed without significant modifications to the reactor system.

In certain embodiments, processed oils, such as blown oils, are the source of fatty acids useful herein. Blown oils are processed through partial oxidation. Common blown oils available include linseed oil, castor oil, fish oil, and soybean oil.

Natural oils may be further processed before use in the present invention, for example, natural oils may be esterified with alcohols to convert any fatty acids present to fatty acid esters, to produce biodiesel. Biodiesel is a mixture of mono-alkyl fatty acid esters typically derived from the transesterification of natural oils and alcohols. While natural oils and alcohols are commonly employed as reactants in esterification reactions, any fatty acid source, such as free fatty acids, soaps, esters, glycerides (mono-, di-, and tri-), phospholipids, lysophospholipids, or amides and a monohydric alcohol source, such as an alcohol, can be esterified.

Biodiesel compositions that are particularly useful in this invention are those which have high concentrations of oleic acids, erucic acids, and esters thereof. These fatty acids and esters have one site of unsaturation such that CM with ethylene yields the LAO, 1-decene, as the coproduct. Preferred biodiesel compositions are those produced from natural oils such as canola oil, rapeseed oil, palm oil, and other high oleic or high erucic oils. Particularly preferred natural oils include those having at least 30 mol % combined oleic and erucic fatty acid or esters of all fatty acid and fatty acid esters combined, preferably at least 40%, preferably at least 50%, preferably at least 60%, preferably at least 70%, preferably at least 80%, preferably at least 90%.

In yet other embodiments, biodiesel compositions that are particularly useful in this invention are those which have high concentrations of oleic, erucic, linoleic, and linolenic acids and respective esters thereof. Preferred biodiesel compositions are those produced from vegetable oils such as canola oil, soybean oil, sunflower oil, Jatropha oil, and other oils having a high concentration of oleic, erucic, linoleic, and linolenic acids and respective esters thereof. Particularly preferred vegetable oils include those having at least 50 mol % oleic, erucic, linoleic, and linolenic acids and respective esters thereof of all fatty acid and fatty acid ester chains combined, preferably at least 60%, preferably at least 70%, preferably at least 80%, preferably at least 90%.

Linear Alpha Olefins (LAOS)

The metathesis catalyst may be combined with the lower olefin and renewable feedstream in any manner known in the art. In one embodiment, the metathesis catalysts described herein may be combined directly with the lower olefin and renewable feedstreams to produce alpha-olefins, preferably LAOS, preferably $C_4$ to $C_{24}$ alpha-olefins, preferably $C_4$ to $C_{24}$ LAOS, such as preferably 1-decene, 1-heptene, and/or 1-butene.

Typically, the molar ratio of lower olefin to renewable feedstream (such as unsaturated fatty acid or fatty acid ester) is greater than 0.8:1.0, preferably, greater than 0.9:1.0, greater than 1.0:1.0, greater than 1.5:1.0, greater than 2.0:1.0. Typically, the molar ratio of lower olefin to feed material (such as unsaturated fatty acid or fatty acid ester) is less than 3.0:1.0, preferably, less than 2.0:1.0, less than 1.5:1.0. Depending upon the specific reagents, other molar ratios may also be suitable. When the lower olefin is ethylene, for example, a significantly higher molar ratio can be used, because the self-metathesis of ethylene produces only ethylene again and therefore no undesirable co-product olefins are formed. Accordingly, the molar ratio of ethylene to renewable feedstream may range from greater than 0.8:1 to typically less than 20:1.

Generally, the renewable feedstream comprises unsaturated fatty acid esters and/or unsaturated fatty acids and is provided as a liquid at the process temperature, and it is generally preferred to be used neat, that is, without a diluent or solvent. The use of a solvent usually increases recycle requirements and increases costs. Optionally, however, if desired, a solvent can be employed with the lower olefin and/or renewable feedstream. A solvent may be desirable, for instance, where liquid feed material and lower olefin are not entirely miscible, and both then can be solubilized in a suitable solvent. In certain embodiments, the CM reaction of the lower olefin and the renewable feedstream may be run in a biphasic mixture of solvents, in an emulsion or suspension, or in a lipid vesicle, or bilayer.

Suitable diluents/solvents for the process include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, including those that can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable diluents/solvents also include aromatic hydrocarbons, such as toluene or xylenes, and chlorinated solvents, such as dichloromethane. In a preferred embodiment, the feed for the process comprises 60 vol % solvent or less, based on the total volume of the feed, preferably 40 vol % or less, preferably 20 vol % or less.

The quantity of metathesis catalyst that is employed in the process of this invention is any quantity that provides for an operable metathesis reaction. Preferably, the ratio of moles of renewable feedstream (such as unsaturated fatty acid or fatty acid ester) to moles of metathesis catalyst is typically greater than 10:1; preferably, greater than 100:1; preferably, greater than 1,000:1; preferably, greater than 10,000:1; preferably, greater than 25,000:1; preferably, greater than 50,000:1; preferably, greater than 100,000:1.

In a preferred embodiment, from 0.005 nmoles to 500 nmoles, preferably from 0.1 to 250 nmoles, and most preferably from 1 to 50 nmoles of the metathesis catalyst are charged to the reactor per 3 mmoles of renewable feedstream (such as TAGs, biodiesel, fatty acids, fatty acid esters, and/or fatty acid alkyl esters, or mixtures thereof; preferably, fatty acid esters) charged.

The process may be batch, semi-batch, or continuous. As used herein, the term continuous means a system that operates without interruption or cessation. For example, a continuous process to produce a metathesis product would be one where the reactants are continually introduced into one or more reactors and metathesis products are continually withdrawn.

The processes may be conducted in any of glass lined, stainless steel, or similar type reaction equipment. Useful reaction vessels include reactors (including continuous stirred tank reactors, batch reactors, reactive extruder, pipe, or pump, continuous flow fixed bed reactors, slurry reactors, fluidized bed reactors, and catalytic distillation reactors). The reaction zone may be fitted with one or more internal and/or external heat exchanger(s) in order to control temperature fluctuations.

If the process is conducted in a batch reactor, then the contacting time of the renewable feedstream and catalyst can be of any duration, provided that the desired olefin metathesis products are obtained. Generally, the contacting time in a reactor is greater than 5 minutes; and preferably, greater than 10 minutes. Generally, the contacting time in a reactor is less than 25 hours; preferably, less than 15 hours; and more preferably, less than 10 hours.

In a preferred embodiment, the reactants (for example, metathesis catalyst; renewable feedstream; lower olefin, optional diluent, etc.) are combined in a reaction vessel at a temperature of 20 to 300° C. (preferably, 20 to 200° C.; preferably, 30 to 100° C.; preferably, 40 to 60° C.) and an olefin (such as ethylene) at a pressure of 0.1 to 1000 psi (0.7 kPa to 6.9 MPa) (preferably, 20 to 400 psi (0.14 MPa to 2.8 MPa); preferably, 50 to 250 psi (0.34 MPa to 1.7 MPa)), if the olefin is present, for a residence time of 0.5 seconds to 48 hours (preferably, 0.25 to 5 hours; preferably, 30 minutes to 2 hours).

In certain embodiments, where the olefin is a gaseous olefin, the olefin pressure is greater than 5 psig (34.5 kPa); preferably, greater than 10 psig (68.9 kPa); and more preferably, greater than 45 psig (310 kPa). When a diluent is used with the gaseous olefin, the aforementioned pressure ranges may also be suitably employed as the total pressure of olefin and diluent. Likewise, when a liquid olefin is employed and the process is conducted under an inert gaseous atmosphere, then the aforementioned pressure ranges may be suitably employed for the inert gas pressure.

In a preferred embodiment, the process is typically a solution process, although it may be a bulk or high pressure process. Homogeneous processes are preferred. (A homogeneous process is defined to be a process where at least 90 wt % of the product is soluble in the reaction media.) A bulk homogeneous process is particularly preferred. (A bulk process is defined to be a process where reactant concentration in all feeds to the reactor is 70 vol % or more.) Alternately, no solvent or diluent is present or added in the reaction medium, (except for the small amounts used as the carrier for the catalyst or other additives, or amounts typically found with the reactants, e.g., propane in propylene).

In the process of this invention, the conversion of the renewable feedstream (preferably, fatty acid ester) to the desired LAO products can vary widely depending upon the specific reagents, such as, for example, the lower olefins, the specific metathesis catalyst, the specific process conditions employed, and the specific chemical makeup of the fatty acid ester. For the purpose of this invention, "conversion" is defined as the mole percentage of feed material that is converted to the CM products, that is, LAOS. In some embodiments, the conversion of the renewable feedstream (preferably, fatty acid ester) to LAOs is greater than 50 mol %; preferably, greater than 60 mol %; and more preferably, greater than 70 mol %. In other embodiments, the conversion of the renewable feedstream (preferably, fatty acid ester) to LAOs is greater than 50 mol %; preferably, greater than 60 mol %; and more preferably, greater than 70 mol %.

In the process of this invention, the yields of the LAO can also vary depending upon the specific reagent olefins, catalyst, and process conditions employed. For the purposes of this invention "yield" will be defined as the mole percentage of LAOs formed relative to the initial moles of renewable feedstream (such as, fatty acid ester in the feed). In embodiments where the renewable feedstock comprises TAGs (as represented in the formula below):

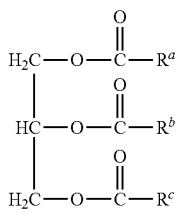

where $R^a$, $R^b$, and $R^c$ each, independently, represent a saturated or unsaturated hydrocarbon chain (preferably, $R^a$, $R^b$, and $R^c$ each, independently, are a $C_{12}$ to $C_{28}$ alkyl or olefin; preferably, $C_{16}$ to $C_{22}$ alkyl or olefin), the yield may be defined as defined by the mole percentage of LAOs formed relative to the initial moles of starting fatty acid ester (unsaturated $R^a$+moles of unsaturated $R^b$+moles of unsaturated $R^c$) introduced into the reactor. Alternatively, the yield may be defined by the mole percentage of LAOs formed relative to the initial moles of starting fatty acid ester. In some embodiments, the yield of LAOs is greater than 30 mol % or more; preferably, greater than 35 mol % or more; preferably, greater than 40 mol % or more; preferably, greater than 45 mol % or more; preferably, greater than 50 mol % or more; preferably, greater than 55 mol % or more; preferably, greater than 60 mol % or more. In some embodiments, the yield of LAOs is greater than 30 mol % or more; preferably, greater than 35 mol % or more; preferably, greater than 40 mol % or more; preferably, greater than 45 mol % or more; preferably, greater than 50 mol % or more; preferably, greater than 55 mol % or more; preferably, greater than 60 mol % or more.

For the purposes of this invention, "productivity" is defined to be the amount in grams of LAO produced per mmol of catalyst introduced into the reactor, per hour. In a preferred embodiment, the productivity of the process is at least 200 g of LAO (such as, decene-1) per mmol of catalyst per hour; preferably, at least 5000 g/mmol/hour; preferably, at least 10,000 g/mmol/hour; preferably, at least 300,000 g/mmol/hour.

For the purposes of this invention, "selectivity" is a measure of conversion of lower olefin and renewable feedstream to the LAO products, and is defined by the mole percentage of LAOs formed relative to the initial moles of lower olefin or renewable feedstream. In a preferred embodiment, the selectivity of the process is at least 20 wt % LAOS, based upon the weight of the material exiting the reactor, preferably, at least 25 wt %; preferably, at least 30 wt %; preferably, at least 35 wt %, preferably, at least 40 wt %; preferably, at least 45 wt %; preferably, at least 50 wt %; preferably, at least 60 wt %; preferably, at least 70 wt %; preferably, at least 80 wt %; preferably, at least 85 wt %; preferably, at least 90 wt %; preferably, at least 95 wt %.

For the purpose of this invention, "catalyst turnover number" (TON) is a measure of how active the catalyst compound is and is defined as the number of moles of LAO formed per mole of catalyst compound. In a preferred embodiment, the (TON) of the process is at least 5,000; preferably, at least 10,000; preferably, at least 50,000; preferably, at least 100,000; preferably, at least 1,000,000.

In a particular embodiment, a fatty acid or a fatty acid ester which is monosaturated may be cross-metathesized with a lower olefin in the presence of metathesis catalysts of the present invention to produce a desired $C_4$ to $C_{40}$ LAO. For example, methyl oleate and ethylene may be cross-metathesized using a suitable metathesis catalyst to produce major CM products of 1-decene and methyl-9-decanoate. Both products are alpha-olefins; however, the decanoate terminates in an ester moiety at the opposite end of the chain from the carbon-carbon double bond. In addition to the major products, the methyl oleate may self-metathesize to produce small amounts of 9-octadecene, a less desirable product, and dimethyl-9-octadecene-1,18-dioate, a second less desirable product.

In yet other embodiments, mixtures of fatty acids, or fatty acid esters, or a natural oil comprising mixtures of monosaturated and polyunsaturated fatty acids and/or esters, or a mixture of natural oils may be cross-metathesized with a lower olefin in the presence of a suitable metathesis catalyst to produce a desired LAO. For example, a mixture of methyl oleate and methyl linoleate may be cross-metathesized with ethylene to produce 1-decene.

Ring-Opening Metathesis Polymerization (ROMP)

In particular embodiments, the present invention involves a process for performing a metathesis reaction, as described above, wherein the at least one olefin comprises at least one cyclic olefin. In such embodiments, the metathesis product comprises a polyolefin.

Cyclic Olefins

The cyclic olefin may be a single cyclic olefin, or a combination of cyclic olefins, that is a mixture of two or more different cyclic olefins. The cyclic olefins may be strained or unstrained, monocyclic, or polycyclic; and may optionally include hetero atoms and/or one or more functional groups. Suitable cyclic olefins include, but are not limited to norbornene, norbornadiene, dicyclopentadiene, cyclopentene, cycloheptene, cyclooctene, cyclooctadiene, cyclododecene, 7-oxanorbornene, 7-oxanorbornadiene, and substituted derivatives therefrom. Illustrative examples of suitable substituents include, but are not limited to, hydroxyl, thiol, ketone, aldehyde, ester, ether, amine, imine, amide, nitro, carboxylic acid, disulfide, carbonate, isocyanate, carbodiimide, carboalkoxy, and halogen. Preferred cyclic olefins include cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives, preferably norbornene, norbornadiene, and dicyclopentadiene, as shown below.

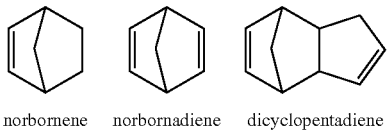

norbornene   norbornadiene   dicyclopentadiene

Polyolefins

The cyclic olefins discussed above may undergo ROMP to form a polyolefin. The ROMP reaction may occur either in the presence or absence of solvent and may optionally include additives. Known additives include antistatics, antioxidants, light stabilizers, plasticizers, dyes, pigments, fillers, reinforcing fibers, lubricants, adhesion promoters, viscosity-increasing agents, and demolding enhancers. Illustrative examples of fillers for improving the optical physical, mechanical and electrical properties include glass and quartz in the form of powders, beads and fibers, metal and semi-metal oxides, carbonates (i.e., $MgCO_3$, $CaCO_3$), dolomite, metal sulfates (such as, gypsum and barite), natural and synthetic silicates (i.e., zeolites, wollastonite, feldspars), carbon fibers, and plastic fibers or powders.

The utility of the inventive catalysts in ROMP reactions was demonstrated with polymerizations of DCPD, NBD, and NB, as shown below, where the metathesis catalyst composition comprised $(Cy_3P)_2Ru(H_2)HCl$, hexachloroethane and, optionally, phenylacetylene, and where n=1 to 100,000, depending on the catalyst loading and the kinetics of the reaction.

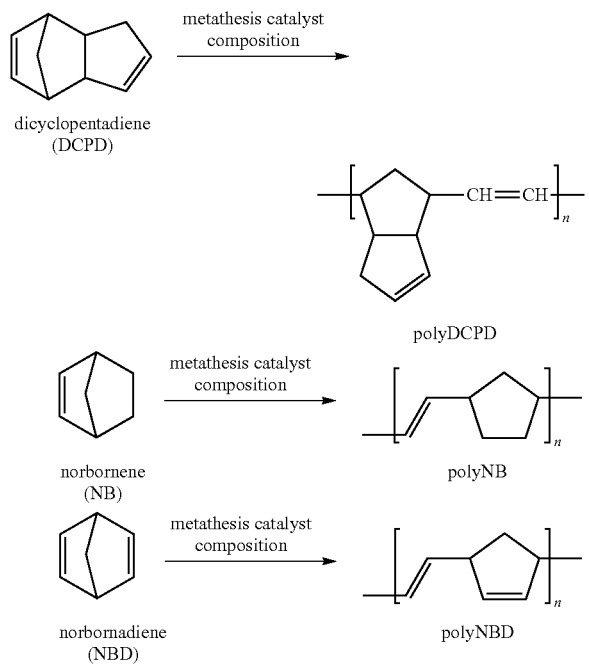

Exposure of neat DCPD to the catalyst composition at a catalyst loading of 10,000:1 (moles DCPD: moles catalyst) of the present invention at room temperature and pressure yielded within minutes a hard, highly-crosslinked material (See Examples 1-4 and 6-8). In fact, catalyst loadings as low as 54,000:1 have been used at room temperature and pressure herein to make a poly-DCPD product (See Example 5).

Ring-Opening Cross Metathesis Polymerization (ROCM)

In particular embodiments, the present invention involves a process for performing a metathesis reaction, as described above, wherein the at least one olefin comprises at least one cyclic olefin and at least one second olefin. In such embodiments, the metathesis product comprises a ROCM product of the cyclic olefin and the second olefin. The wide synthetic availability of cyclic olefins makes this route attractive, and cyclic compounds are particularly important in synthesis. Most significantly, ring systems are key to stereochemical control; the understanding of ring conformation often presents the most expeditious route for stereocenter installation. The ability to take these general carbocycles to highly functionalized linear molecules (which, ideally, would have differentially protected termini) would be extremely valuable to the synthetic chemist.

Cyclic Olefins

The cyclic olefin may be a single cyclic olefin, or a combination of cyclic olefins, that is a mixture of two or more different cyclic olefins, as described above.

Second Olefins

Any olefin may be used for the ROCM reaction with the at least one cyclic olefin. For example, a terminal olefin may be used. For the purposes of this invention and the claims thereto, the term "terminal olefin" refers to an organic compound containing at least one carbon-carbon double bond, where the at least one carbon-carbon double bond occurs between the alpha and beta carbons of the chain. Terminal olefins may be represented by the formula: $H_2C$=$CH$—$R^*$, wherein each $R^*$ is independently, hydrogen or a $C_1$ to $C_{30}$ hydrocarbyl; preferably, a $C_2$ to $C_{20}$ hydrocarbyl; preferably, a $C_2$ to $C_{12}$ hydrocarbyl; preferably, methyl, ethyl, propyl, butyl, pentyl, hexyl, and substituted and cyclic analogs thereof. For example, 1-hexene, 1-heptene, and 1-decene are terminal olefins that are particularly useful in embodiments herein.

In other embodiments internal olefins may be used. For the purposes of this invention and the claims thereto, the term "internal olefin" refers to an organic compound containing at least one carbon-carbon double bond, where the at least one carbon-carbon double bond does not occur between the alpha and beta carbons of the chain. Internal olefins may be represented by the formula: $R^*HC$=$CH$—$R^*$, wherein each $R^*$ is independently, a $C_1$ to $C_{30}$ hydrocarbyl; preferably, a $C_2$ to $C_{20}$ hydrocarbyl; preferably, a $C_2$ to $C_{12}$ hydrocarbyl; preferably, methyl, ethyl, propyl, butyl, pentyl, hexyl, and substituted and cyclic analogs thereof. For example, hex-2-ene, hept-3-ene, and TBS-protected 4-penten-1-ol (TBS means "tert-butyl silyl") are particularly useful in embodiments herein.

Polyolefin

ROCM involves a tandem sequence in which a cyclic olefin is opened and a second, acyclic olefin is crossed onto the newly formed termini. After the initial ring opening event, the Group 8 metal-bound intermediate has two options: reaction with another cyclic olefin or reaction with the other olefin. It will be appreciated that a ROCM reaction between a cyclic olefin and a second olefin reactant can result in several different types of reaction products, depending, in large part, on the relative rates of the ring-opening metathesis reaction and the cross-metathesis reaction between the second olefinic reactant and the cyclic olefin, as shown in FIG. 1; where n=1 to 100,000 and R is a $C_1$ to $C_{30}$ hydrocarbyl, derived from the second olefin; preferably, a $C_2$ to $C_{20}$ hydrocarbyl; preferably, a $C_2$ to $C_{12}$ hydrocarbyl; preferably, methyl, ethyl, propyl, butyl, pentyl, hexyl, and substituted and cyclic analogs thereof.

Accordingly, a cyclic olefin will undergo a ring opening reaction in the presence of the catalyst at a rate constant $k_{RO}$, and the second olefin reactant will undergo a cross-metathesis reaction with the ring opened cyclic olefin at a rate constant $k_{CM}$. When $k_{CM}$ is greater than or equal to $k_{RO}$, the ROCM product is predominantly a monomer, dimer, and/or oligomer, but not a polymer. More specifically, when $k_{CM}$ is approximately equal to $k_{RO}$, the ROCM product is predominantly a dimer or oligomer, while when $k_{RO}$ is greater than $k_{CM}$, the ROCM product is predominantly a polymer. Dimers and oligomers are of particular interest because their internal olefin moieties may be further functionalized by metathesis or other transformations.

Monomers are also of interest, particularly when they can be prepared so as to be end differentiated, i.e., asymmetric with regard to the two terminal olefinic groups resulting from the ROCM reaction. It should be appreciated that $k_{RO}$ will be higher for moderately and highly strained cyclic olefins such as cyclooctadiene, but lower for low-strain olefins such as cyclopentene and cyclohexene.

For example, the ROCM of norbornadiene and 1-decene in the presence of the catalysts described herein produces decene-capped oligomers of oligo(norbornadiene) (Example 21), as shown in the scheme below:

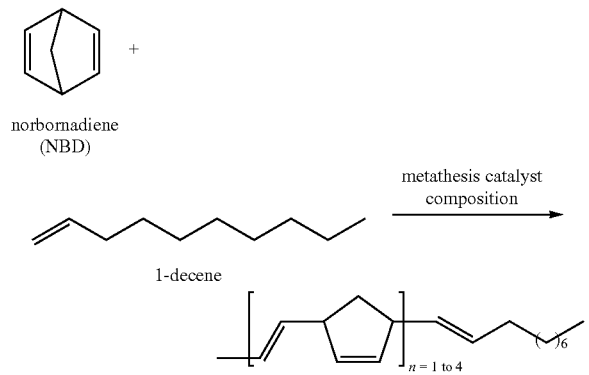

where the metathesis catalyst composition comprises $(Cy_3P)_2Ru(H_2)HCl$, hexachloroethane, and, optionally, phenylacetylene.

The choice of the cyclic olefin and the second olefin used in a ROCM reaction may allow for tailoring of the resultant capped poly(cyclic olefin). Use of olefins with protected functionalities, for example, TBS-protected 4-penten-1-ol, may allow for introduction of functional groups to the capped poly(cyclic olefin). Some examples of functionalized poly(cyclic olefin)s include those that are functionalized with maleic acid or maleic anhydride groups.

The functionalized capped poly(cyclic olefin) can in turn be derivatized with a derivatizing compound, such as described in U.S. Pat. No. 6,022,929; A. Toyota, T. Tsutsui, and N. Kashiwa, Polymer Bulletin 48, 213-219, 2002; and J. Am. Chem. Soc., 1990, 112, 7433-7434. The derivatizing compound can react with the functional groups of the functionalized capped poly(cyclic olefin) by any means known in the art, such as nucleophilic substitution, Mannich Base condensation, and the like. The derivatizing compound can be polar and/or contain reactive derivative groups. Preferred derivatizing compounds are selected from hydroxy containing compounds, amines, metal salts, anhydride containing compounds, and acetyl halide containing compounds. The derivatizing compounds can comprise at least one nucleophilic group and preferably at least two nucleophilic groups. An exemplary derivatized capped poly(cyclic olefin) may be made by contacting a functionalized capped poly(cyclic olefin), for example, one substituted with a carboxylic acid/anhydride or ester, with a nucleophilic reagent, for example, amines, alcohols (including polyols), amino alcohols, reactive metal compounds and the like. (For more information please see U.S. Pat. No. 6,022,929, column 33, line 27 to column 74, line 63.)

In another embodiment, this invention relates to:

1. A metathesis catalyst comprising:

i. a Group 8 metal hydride-dihydrogen complex represented by the formula:

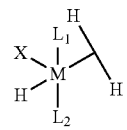

wherein

M is a Group 8 metal; preferably, M is ruthenium or osmium;

X is an anionic ligand; preferably, selected from the group consisting of halides, alkoxides, aryloxides, and alkyl sulfonates; and $L_1$ and $L_2$ are neutral donor ligands; preferably, $L_1$ and $L_2$ are independently selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof; preferably, at least one of $L_1$ and $L_2$ is selected from a phosphine, an N-heterocyclic carbene, a cyclic alkyl amino carbene, and substituted analogs thereof; and ii. a ligand exchange agent represented by the formula J-Y; wherein J is selected from the group consisting of hydrogen, a $C_1$ to $C_{30}$ hydrocarbyl, and a $C_1$ to $C_{30}$ substituted hydrocarbyl; and Y is selected from the group consisting of halides, alkoxides, aryloxides, and alkyl sulfonates; preferably, Y is a halide; preferably, Y is chloride.

2. The metathesis catalyst composition of paragraph 1, wherein the Group 8 metal hydride-dihydrogen complex is selected from (1,3-bis-(2,4,6-trimethylphenyl)-2-(imidazolidinylidene)(tricyclohexylphosphine)(dihydrogen)rutheniumhydridochloride, bis-(tricyclohexylphosphine)(dihydrogen)rutheniumhydridochloride, (1-mesityl-3-methyl-2H-4,5-dihydroimidazol-2-ylidene)(tricyclohexylphosphine)-(dihydrogen) rutheniumhydridochloride, and 2-(2,6-diethylphenyl)-3,3,5,5-tetramethylpyrrolidine-(tricyclohexylphosphine)-(dihydrogen) rutheniumhydridochloride.

3. The metathesis catalyst composition of paragraphs 1 or 2, wherein the ligand exchange agent is selected from tetrachloroethane, pentachloroethane, hexachloroethane; preferably, pentachloroethane or hexachloroethane 4. The metathesis catalyst composition of any of paragraphs 1 to 3, further comprising an acetylene compound represented by the formula:

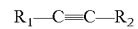

wherein $R_1$ and $R_2$ are independently selected from the group consisting of hydrogen, a $C_1$ to $C_{30}$ hydrocarbyl, and a $C_1$ to $C_{30}$ substituted hydrocarbyl; preferably, at least one of $R_1$ and $R_2$ is hydrogen; preferably, the acetylene compound is acetylene or phenylacetylene.

5. A method for making the metathesis catalyst composition of paragraph 1 to 3, comprising:
contacting the Group 8 metal hydride-dihydrogen complex with the ligand exchange agent.

6. The method of paragraph 5, further comprising contacting the Group 8 metal hydride-dihydrogen complex and the ligand exchange agent with an acetylene compound represented by the formula:

wherein $R_1$ and $R_2$ are independently selected from the group consisting of hydrogen, a $C_1$ to $C_{30}$ hydrocarbyl, and a $C_1$ to $C_{30}$ substituted hydrocarbyl; preferably, at least one of $R_1$ and $R_2$ is hydrogen; preferably, the acetylene compound is acetylene or phenylacetylene.

7. A process for performing a metathesis reaction comprising:
contacting at least one olefin with a metathesis catalyst;
wherein the metathesis catalyst comprises a Group 8 metal hydride-dihydrogen complex represented by the formula:

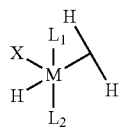

wherein
M is a Group 8 metal; preferably, M is ruthenium or osmium;
X is an anionic ligand; preferably, selected from the group consisting of halides, alkoxides, aryloxides, and alkyl sulfonates; and
$L_1$ and $L_2$ are neutral donor ligands; preferably, $L_1$ and $L_2$ are independently selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof; preferably, at least one of $L_1$ and $L_2$ is selected from a phosphine, an N-heterocyclic carbene, a cyclic alkyl amino carbene, and substituted analogs thereof.

8. The process of paragraph 7, wherein the Group 8 metal hydride-dihydrogen complex is selected from (1,3-bis-(2,4,6-trimethylphenyl)-2-(imidazo lidinylidene) (tricyclohexylphosphine)(dihydrogen)rutheniumhydridochloride, bis-(tricyclohexylphosphine) (dihydrogen)rutheniumhydridochloride, (1-mesityl-3-methyl-2H-4,5-dihydroimidazol-2-ylidene)(tricyclohexylphosphine)-(dihydrogen)ruthenium-hydridochloride, and 2-(2,6-diethylphenyl)-3,3,5,5-tetramethylpyrrolidine-(tricyclohexylphosphine)(dihydrogen)rutheniumhydridochloride.

9. A process for performing a metathesis reaction comprising: contacting at least one olefin with the metathesis catalyst composition of paragraphs 1 to 3.

10. The process of paragraph 9, wherein the metathesis catalyst further comprises an acetylene compound represented by the formula:

wherein $R_1$ and $R_2$ are independently selected from the group consisting of hydrogen, a $C_1$ to $C_{30}$ hydrocarbyl, and a $C_1$ to $C_{30}$ substituted hydrocarbyl; preferably, at least one of $R_1$ and $R_2$ is hydrogen; preferably, the acetylene compound is acetylene or phenylacetylene.

11. The process of any of paragraphs 7 to 10, wherein the at least one olefin comprises (i) at least one renewable feedstream selected from canola oil, corn oil, soybean oil, rapeseed oil, algae oil, peanut oil, mustard oil, sunflower oil, tung oil, tall oil, perilla oil, grapeseed oil, linseed oil, safflower oil, pumpkin oil, palm oil, Jatropha oil, high-oleic soybean oil, high-oleic safflower oil, high-oleic sunflower oil, mixtures of animal and vegetable fats and oils, beef tallow, castor bean oil, dehydrated castor bean oil, cucumber oil, poppyseed oil, flaxseed oil, lesquerella oil, walnut oil, cottonseed oil, meadowfoam, tuna oil, sesame oils, waste oils/greases and mixtures thereof; and (ii) at least one lower olefin having the formula $R^*—HC=CH—R^*$, wherein each $R^*$ is independently hydrogen or a $C_1$ to $C_2$ hydrocarbyl, and wherein a linear alpha olefin is produced.

12. The process of any of paragraphs 7 to 10, wherein the at least one olefin comprises at least one cyclic olefin, selected from cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, and norbornadiene; and wherein a polyolefin is produced.

13. The process of any of paragraphs 7 to 10, wherein the at least one olefin is a linear alpha olefin, and wherein the linear alpha olefin is isomerized to internal isomers thereof.

Experimental Section

For purposes of this invention and the claims thereto, Cy is cyclohexyl, DCM is dichloromethane, DCPD is dicyclopentadiene, NB is norbornene, NBD is norbornadiene, HCE is hexachloroethane, PCE is pentachloroethane, and PhAc is phenyl acetate.

Tests and Materials

Typical dry-box procedures for synthesis of air-sensitive compounds were followed, including using dried glassware (90° C., 4 hours) and using anhydrous solvents purchased from Sigma Aldrich (St. Louis, Mo.), which were further dried over 3 A sieves. All reagents were purchased from Sigma-Aldrich and used as received, unless otherwise noted. 1-hexene was obtained from Aldrich and dried over a NaK alloy prior to use.

$^1H$ and $^{31}P$ spectra were recorded on Bruker 250 and 500 spectrometers. Yields of total internal olefins were derived from $^1H$ NMR spectra.

Products were analyzed by gas chromatography (Agilent 6890N with auto-injector) using helium as a carrier gas at 38 cm/sec. A column having a length of 60 m (J & W Scientific DB-1, 60 m×0.25 mm I.D.×1.0 μm film thickness) packed with a flame ionization detector (FID), an Injector temperature of 250° C., and a Detector temperature of 250° C. were used. The sample injected into the column in an oven at 70° C., then heated to 275° C. over 22 minutes (ramp rate 10° C./min to 100° C., 30° C./min to 275° C., hold). Yields of metathesis product were calculated from the data recorded on an Agilent 6890 GC spectrometer, as shown below.

Typically, a sample of the metathesis product will be taken and analyzed by GC. An internal standard, usually tetradecane, is used to derive the amount of metathesis product that is obtained. The amount of metathesis product is calculated from the area under the desired peak on the GC trace, relative to the internal standard. Yield or conversion is reported as a percentage and defined as 100×[micromoles of metathesis products obtained by GC]/[micromoles of feed material weighed into reaction vessel].

Yields of isomerized product were obtained by subtraction of the yield of metathesis product obtained (determined from GC spectra, above) from the yield of total internal olefins (determined from $^1H$ NMR data, above).

NMR Studies of the Ligand Exchange Agent $^1$H and $^{31}$P NMR experiments were performed to investigate the behavior of the ligand exchange agents pentachloroethane and hexachloroethane in the presence of a Group 8 metal hydride-dihydrogen complex, and under metathesis conditions. The Group 8 metal hydride-dihydrogen complex used was $RuClH(H_2)(PCy_3)_2$.

Reaction of $Cy_3P$ with Hexachloroethane. Tricyclohexylphosphine (0.1 grams) was combined with hexachloroethane (0.1 grams) in two milliliters of deuterated dichloromethane. After 10 minutes of stirring, the solution was analyzed by $^{31}$P NMR spectroscopy. The spectrum showed the synthesis of $Cy_3PCl_2$. $^{31}$P NMR ($CD_2Cl_2$): δ 107.4.

Reaction of $Cy_3P$ with Pentachloroethane. Tricyclohexylphosphine (0.020 grams) was combined with pentachloroethane (0.1 grams) in two milliliters of deuterated dichloromethane. After 10 minutes of stirring, the solution was analyzed by $^{31}$P NMR spectroscopy. The spectrum showed the synthesis of $Cy_3PCl_2$. $^{31}$P NMR ($CD_2Cl_2$): δ 107.3.

Reaction of Hexachloroethane and $(Cy_3P)_2Ru(H_2)HCl$. A 0.1 gram amount of $(Cy_3P)_2Ru(H_2)HCl$ was combined with a 0.2 gram amount of hexachloroethane in deuterated dichloromethane. Upon mixing, the solution turned green. Analysis by $^{31}$P NMR spectroscopy was performed yielding the following peaks: $^{31}$P NMR ($CD_2Cl_2$): δ 117.4, 107.9 ($Cy_3PCl_2$), 92.3 (br). The spectrum indicates that hexachloroethane is capable of phosphine abstraction from $(Cy_3P)_2Ru(H_2)HCl$ through an oxidation pathway, forming $Cy_3PCl_2$ as a byproduct.

Observation of $Cy_3PCl_2$ formation in Ring-Opening Metathesis Polymerizations. A 2.0 mg amount of $(Cy_3P)_2Ru(H_2)HCl$ and 5 equivalents of hexachloroethane (3.5 mg) were added to a 20 mL scintillation vial along with 1.0 mL of $CD_2Cl_2$. This solution was added to an NMR tube along with 2 pipetted drops of dicyclopentadiene. Analysis by $^{31}$P NMR spectroscopy was performed yielding the following peaks: $^{31}$P NMR ($CD_2Cl_2$): δ 118, 109 ($Cy_3PCl_2$).

EXAMPLES

Ring-Opening Metathesis Polymerization (ROMP)

Catalyst compositions described herein were used for the ROMP of DCPD (dicyclopentadiene), norbornadiene (NBD or bicyclo[2.2.1]hepta-2,5-diene), or norbornene (NB or bicyclo[2.2.1]hept-2-ene). The Group 8 metal hydride-dihydrogen complex used was $RuClH(H_2)(PCy_3)_2$, which was prepared as described in Organometallics 1997, 16, 3867. The ligand exchange agent used was hexachloroethane or pentachloroethane. The acetylene used was phenylacetylene.

General Procedure for Ring-Opening Metathesis Polymerization (ROMP)

Approximately 10 g of at least one olefin was charged to a reaction vessel. The Group 8 metal hydride-dihydrogen complex described herein was added to the reaction vessel, as a solution in DCM. Optionally, a ligand exchange agent was added to the reaction vessel. Further, an acetylene may be optionally charged to the reaction vessel. Experiments were performed at room temperature. The solution was observed over the first ten minutes, and then again after 24 hours, and any visual observations recorded.

Example 1

ROMP of DCPD: A 10.0 gram (75.6 mmol) amount of dicyclopentadiene was added to a 20 ml scintillation vial. A 5.0 milligram (7.2 μmol) amount of $RuClH(H_2)(PCy_3)_2$ was added. One equivalent of phenylacetylene and hexachloroethane per equivalent of $RuClH(H_2)(PCy_3)_2$ was charged via the addition of 0.1 mls each of a 72 mM stock solution of phenylacetylene and hexachloroethane, respectively. The ring opening polymerization of dicyclopentadiene was observed by a gradual thickening of the solution to a rubbery viscous material after six minutes. After one hour a solid rubbery material had formed.

Example 2

ROMP of DCPD: A 10.0 gram (75.6 mmol) amount of dicyclopentadiene was added to a 20 ml scintillation vial. A 5.0 milligram (7.2 μmol) amount of $RuClH(H_2)(PCy_3)_2$ was added. Five equivalents of phenylacetylene and hexachloroethane per equivalent of $RuClH(H_2)(PCy_3)_2$ were added via the addition of 0.5 mls of 72 mM solution of phenylacetylene and hexachloroethane, respectively. The ring-opening polymerization of dicyclopentadiene was observed by a rapid thickening of the solution to a rubbery viscous material. After 4 minutes, the material was a rubbery solid. After 24 hours, the material was a hard rubbery solid.

Example 3

ROMP of DCPD: A 10.0 gram (75.6 mmol) amount of dicyclopentadiene was added to a 20 ml scintillation vial. A 5.0 milligram (7.2 μmol) amount of $RuClH(H_2)(PCy_3)_2$ was added. One equivalent of phenylacetylene per equivalent of $RuClH(H_2)(PCy_3)_2$ was added via the addition of 0.1 mls of 72 mM solution of phenylacetylene. Ten equivalents of hexachloroethane per equivalent of $RuClH(H_2)(PCy_3)_2$ were charged via the addition of 1.0 mls of a 72 mM solution. The ring opening polymerization of dicyclopentadiene was observed by a gradual thickening of the solution to a rubbery viscous material after six minutes. After one hour, a solid rubbery material had formed.

Example 4

ROMP of DCPD: A 10.0 gram (75.6 mmol) amount of dicyclopentadiene was added to a 20 ml scintillation vial. A 5.0 milligram (7.2 μmol) amount of $RuClH(H_2)(PCy_3)_2$ was added. Ten equivalents of phenylacetylene and hexachloroethane per equivalent of $RuClH(H_2)(PCy_3)_2$ were added via the addition of 1.0 mls each of a 72 mM solution of phenylacetylene and hexachloroethane, respectively. The ring opening polymerization of dicyclopentadiene was observed by a rapid thickening of the solution to a rubbery viscous material. After 4 minutes, the material was a rubbery solid. After 24 hours, a hard rubbery solid was obtained.

Example 5

ROMP of DCPD: A 10.0 gram (75.6 mmol) amount of dicyclopentadiene was added to a 20 ml scintillation vial. A 1.2 milligram (1.7 μmol) amount of $RuClH(H_2)(PCy_3)_2$ was added. One equivalent of phenylacetylene per equivalent of $RuClH(H_2)(PCy_3)_2$ was added via the addition of 0.1 mls of 72 mM solution of phenylacetylene. 100 equivalents of hexachloroethane (170 mg) was added. The ring opening polymerization of dicyclopentadiene was observed slowly by a gradual thickening of the solution to a rubbery viscous material after three hours. After 24 hours, the material was a gel-like.

Example 6

ROMP of DCPD: A 10.0 gram (75.6 mmol) amount of dicyclopentadiene was added to a 20 ml scintillation vial. A 5.0 milligram (7.2 μmol) amount of $RuClH(H_2)(PCy_3)_2$ was added. The ring opening polymerization of dicyclopentadiene was observed slowly by a gradual thickening of the solution to a rubbery viscous material after three hours. After 24 hours, the material was a soft rubbery material.

Example 7

ROMP of DCPD: A 10.0 gram (75.6 mmol) amount of dicyclopentadiene was added to a 20 ml scintillation vial. A 5.0 milligram (7.2 µmol) amount of $RuClH(H_2)(PCy_3)_2$ was added. One equivalent of phenylacetylene per equivalent of $RuClH(H_2)(PCy_3)_2$ was added via the addition of 0.1 mls of a 72 mM solution of phenylacetylene. The ring opening polymerization of dicyclopentadiene was observed slowly by a gradual thickening of the solution to a rubbery viscous material after three hours. After 24 hours, the material was soft and rubbery.

Example 8

ROMP of DCPD: A 10.0 gram (75.6 mmol) amount of dicyclopentadiene was added to a 20 ml scintillation vial. A 5.0 milligram (7.2 µmol) amount of $RuClH(H_2)(PCy_3)_2$ was added. One equivalent of hexachloroethane was charged per equivalent of $RuClH(H_2)(PCy_3)_2$ via the addition of 0.1 mls of a 72 mM hexachloroethane solution. The ring opening polymerization of dicyclopentadiene was observed slowly by a gradual thickening of the solution to a rubbery viscous material after three hours. After 24 hours, the material was a soft rubbery material.

Example 9

ROMP of DCPD: A 10.0 gram (75.6 mmol) amount of dicyclopentadiene was added to a 100 ml round-bottom flask. A 5.0 milligram (7.2 µmol) amount of $RuClH(H_2)(PCy_3)_2$, ten equivalents of hexachloroethane, and ten equivalents of phenylacetylene were added via the addition of a 0.5 mls stock solution containing 2.5 mls of $CH_2Cl_2$, 25 mg $RuClH(H_2)(PCy_3)_2$, 86 mg of hexachloroethane and 36 mg of phenylacetylene. The ring opening polymerization of dicyclopentadiene was observed slowly by a gradual thickening of the solution to a rubbery viscous material after three hours. After 24 hours, it had become a soft rubbery material.

Example 10

ROMP of Norbornadiene: A 10.0 gram (108 mmol) amount of bicyclo[2.2.1]hepta-2,5-diene was added to a 100 mL round-bottom flask. A 5.0 milligram (7.2 µmol) amount of $RuClH(H_2)(PCy_3)_2$, ten equivalents of hexachloroethane and ten equivalents of phenylacetylene were added. The materials was very viscous after two minutes at which point the material foamed and became a sponge-like material.

Example 11

ROMP of Norbornadiene: A 10.0 gram (108 mmol) amount of bicyclo[2.2.1]hepta-2,5-diene was added to a 100 mL round-bottom flask. A 5.0 milligram (7.2 µmol) amount of $RuClH(H_2)(PCy_3)_2$, ten equivalents of pentachloroethane and ten equivalents of phenylacetylene were added. The material became very viscous after two minutes, at which point the material foamed and became sponge-like.

Example 12

ROMP of Norbornene: A 10.0 gram (106 mmol) amount of bicyclo[2.2.1]hept-2-ene was added to a 100 mL round-bottom flask. A 5.0 milligram (7.2 µmol) amount of $RuClH(H_2)(PCy_3)_2$, ten equivalents of hexachloroethane and ten equivalents of phenylacetylene were added. Immediately upon the dropwise addition of the catalyst solution, a sponge-like rubbery material formed. Twenty minutes after catalyst addition all the monomer had been converted into the rubbery material.

TABLE 2

Summary Of ROMP Reactions Using Metathesis Catalysts

| Examples (Monomer) | Catalyst loading/ (mol monomer: mol catalyst) | Ligand exchange Agent/molar equivalents | | Acetylene (PhAc)/molar equivalents | Visual Observations Of Polymer |
|---|---|---|---|---|---|
| | | HCE | PCE | | |
| 1 (DCPD) | 10,500:1 | 1 | 0 | 1 | 6 mins: viscous<br>1 hr: hard |
| 2 (DCPD) | 10,500:1 | 5 | 0 | 5 | 4 mins: viscous<br>24 hrs: hard |
| 3 (DCPD) | 10,500:1 | 10 | 0 | 1 | 6 mins: viscous<br>1 hr: hard |
| 4 (DCPD) | 10,500:1 | 10 | 0 | 10 | 4 mins: viscous<br>24 hrs: hard |
| 5 (DCPD) | 54,000:1 | 100 | 0 | 1 | 3 mins: viscous<br>24 hrs: gel-like |
| 6 (DCPD) | 10,500:1 | 0 | 0 | 0 | 3 hrs: viscous<br>24 hrs: soft |
| 7 (DCPD) | 10,500:1 | 0 | 0 | 1 | 3 hrs: viscous<br>24 hrs: soft |
| 8 (DCPD) | 10,500:1 | 1 | 0 | 0 | 3 hrs: viscous<br>24 hrs: soft |
| 9 (DCPD) | 10,500:1 | 10 | 0 | 10 | 3 hrs: viscous<br>24 hrs: soft |
| 10 (NBD) | 15,000:1 | 10 | 0 | 10 | 2 mins: viscous<br>24 hrs: spongy. |
| 11 (NBD) | 15,000:1 | 0 | 10 | 10 | 2 mins: viscous<br>24 hrs: spongy. |
| 12 (NB) | 14,722:1 | 10 | 0 | 10 | 2 mins: spongy. |

KEY: Monomers: NBD = norbornadiene, NB = norbornene, DCPD = dicyclopentadiene, Acetylene: PhAc = phenylacetylene, Ligand Exchange Agent: HCE = hexachloroethane, PCE = pentachloroethane Cross Metathesis (CM)

Catalyst compositions described herein were used for the CM of 1-hexene to cis/trans-5-decene. The Group 8 metal hydride-dihydrogen complex used was $RuClH(H_2)(PCy_3)_2$, which was prepared as described in Organometallics 1997, 16, 3867. The ligand exchange agent used was hexachloroethane. The acetylene used was phenylacetylene.

General Procedure for Cross Metathesis (CM)

Approximately 10 g of 1-hexene was charged to a reaction vessel. The Group 8 metal hydride-dihydrogen complex described herein was added to the reaction vessel, as a solution in DCM. Optionally, a ligand exchange agent, hexachloroethane, was added to the reaction vessel. Further, an acetylene, phenylacetylene, may be optionally charged to the reaction vessel. Reactions were conducted at room temperature. Conversion (cis/trans metathesis product yield) and isomerization (internal olefin) percentages were obtained by GC and $^1H$ NMR analysis. The solution was observed over a ten minute time period, and then again after 24 hours, and any visual observations recorded.

Example 13

Cross-metathesis of 1-hexene. A 10.0 gram (119 mmoles) amount of 1-hexene was added to a 20 ml scintillation vial. A 5.0 milligram (7.2 µmol) amount of $RuClH(H_2)(PCy_3)_2$ was added. One equivalent of phenylacetylene and hexachloroethane per equivalent of $RuClH(H_2)(PCy_3)_2$ was charged to the vial via the addition of 0.1 mls each of a 72 mM solution of phenylacetylene and hexachloroethane, respectively. The conversion to cis/trans-5-decene was monitored by GC & $^1H$ NMR. The reactions were performed at room temperature and sampled after two days stirring. Isomerization of 1-hexene to internal olefins was observed as well as some cross metathesis: cis/trans-5-decene 4.6% yield; internal olefins 12.1% yield.

Example 14

Cross-metathesis of 1-hexene. A 10.0 gram (119 mmoles) amount of 1-hexene was added to a 20 ml scintillation vial. A 5.0 milligram (7.2 µmol) amount of $RuClH(H_2)(PCy_3)_2$ was added. Five equivalents of phenylacetylene and hexachloroethane per equivalent of $RuClH(H_2)(PCy_3)_2$ were added via the addition of 0.1 mls each of a 72 mM solution of phenylacetylene and hexachloroethane, respectively. The conversion to cis/trans-5-decene was monitored by GC & $^1H$ NMR. The reactions were performed at room temperature and sampled after two days stirring. Isomerization of 1-hexene to internal olefins was observed as well as some cross metathesis: cis/trans-5-decene 5.6% yield; internal olefins 19.3% yield.

Example 15

Cross-metathesis of 1-hexene. A 10.0 gram (119 mmoles) amount of 1-hexene was added to a 20 ml scintillation vial. A 5.0 milligram (7.2 µmol) amount of $RuClH(H_2)(PCy_3)_2$ was added. One equivalent of phenylacetylene per equivalent of $RuClH(H_2)(PCy_3)_2$ was added via the addition of 0.1 mls of a 72 mM solution of phenylacetylene. Ten equivalents of hexachloroethane per equivalent of $RuClH(H_2)(PCy_3)_2$ was added via the addition 1.0 mls of a 72 mM solution. The conversion to cis/trans-5-decene was monitored by GC & $^1H$ NMR. The reactions were performed at room temperature and sampled after two days stirring. Isomerization of 1-hexene to internal olefins was observed as well as some cross metathesis: cis/trans-5-decene 5.7% yield; internal olefins 20.7% yield.

Example 16

Cross-metathesis of 1-hexene. A 10.0 gram (119 mmoles) amount of 1-hexene was added to a 20 ml scintillation vial. A 5.0 milligram (7.2 µmol) amount of $RuClH(H_2)(PCy_3)_2$ was added. Ten equivalents of phenylacetylene and hexachloroethane per equivalent of $RuClH(H_2)(PCy_3)_2$ were added via the addition of 1.0 mls each of a 72 mM solution of phenylacetylene and hexachloroethane, respectively. The conversion to cis/trans-5-decene was monitored by GC & $^1H$ NMR. The reactions were performed at room temperature and sampled after two days stirring. Isomerization of 1-hexene to internal olefins was observed as well as some cross metathesis: cis/trans-5-decene 7.4% yield; internal olefins 31% yield.

Example 17

Cross-metathesis of 1-hexene. A 10.0 gram (119 mmoles) amount of 1-hexene was added to a 20 ml scintillation vial. A 1.2 milligram (1.4 µmol) amount of $RuClH(H_2)(PCy_3)_2$ was added. One equivalent of phenylacetylene per equivalent of $RuClH(H_2)(PCy_3)_2$ was added via the addition of 0.1 mls of a 72 mM solution of phenylacetylene. One hundred equivalents of hexachloroethane (170 mg) per equivalent of $RuClH(H_2)(PCy_3)_2$ were added. The conversion to cis/trans-5-decene was monitored by GC & $^1H$ NMR. The reactions were performed at room temperature and sampled after two days stirring. Isomerization of 1-hexene to internal olefins was observed as well as some cross metathesis: cis/trans-5-decene 4.5% yield; internal olefins 8.6% yield.

Example 18

Cross-metathesis of 1-hexene. A 10.0 gram (119 mmoles) amount of 1-hexene was added to a 20 ml scintillation vial. A 5.0 milligram (7.2 µmol) amount of $RuClH(H_2)(PCy_3)_2$ was added. The conversion to cis/trans-5-decene was monitored by GC & $^1H$ NMR. The reactions were performed at room temperature and sampled after two days stirring. Isomerization of 1-hexene to internal olefins was observed as well as some cross metathesis: cis/trans-5-decene 2.2% yield; internal olefins 11.9% yield.

Example 19

Cross-metathesis of 1-hexene. A 10.0 gram (119 mmoles) amount of 1-hexene was added to a 20 ml scintillation vial. A 5.0 milligram (7.2 µmol) amount of $RuClH(H_2)(PCy_3)_2$ was added. One equivalent of phenylacetylene per equivalent of $RuClH(H_2)(PCy_3)_2$ was added via the addition of 0.1 mls of a 72 mM solution of phenylacetylene. The conversion to cis/trans-5-decene was monitored by GC & $^1H$ NMR. The reactions were performed at room temperature and sampled after two days stirring. Isomerization of 1-hexene to internal olefins was observed as well as some cross metathesis: cis/trans-5-decene 3.4% yield, internal olefins 13.5% yield.

Example 20

Cross-metathesis of 1-hexene. A 10.0 gram (119 mmoles) amount of 1-hexene was added to a 20 ml scintillation vial. A 5.0 milligram (7.2 µmol) amount of $RuClH(H_2)(PCy_3)_2$ was added. One equivalent of hexachloroethane was added via the addition of 0.1 mls of a 72 mM hexachloroethane solution. The conversion to cis/trans-5-decene was monitored by GC & $^1$H NMR. The reactions were performed at room temperature and sampled after two days stirring. Isomerization of 1-hexene to internal olefins was observed as well as some cross metathesis: cis/trans-5-decene 2.1% yield; internal olefins 10.2% yield.

TABLE 3

Summary Of CM Reactions Using Metathesis Catalysts

| Example | Catalyst Loading/ (mol monomer: mol catalyst) | Ligand Exchange Agent (HCE)/ equivalents | Acetylene (PhAc)/ equivalents | Conversion/ mol % | Isomerization/ mol % |
|---|---|---|---|---|---|
| 13 | 16,528:1 | 1 | 1 | 4.6 | 12.1 |
| 14 | 16,528:1 | 5 | 5 | 5.6 | 19.3 |
| 15 | 16,528:1 | 10 | 1 | 5.7 | 20.7 |
| 16 | 16,528:1 | 10 | 10 | 7.4 | 31.0 |
| 17 | 85,000:1 | 100 | 1 | 4.5 | 8.6 |
| 18 | 16,528:1 | 0 | 0 | 2.2 | 11.9 |
| 19 | 16,528:1 | 0 | 1 | 3.4 | 13.5 |
| 20 | 16,528:1 | 1 | 0 | 2.1 | 10.2 |

KEY: Ligand exchange agent: HCE = hexachloroethane; Acetylene: PhAc = phenylacetylene Ring-Opening Cross Metathesis (ROCM)

Catalyst compositions described herein were used for the ROCM of norbornadiene and 1-decene to decene-capped oligomers of norbornadiene, as shown below:

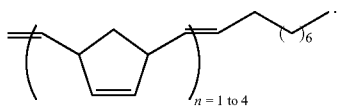

The Group 8 metal hydride-dihydrogen complex used was $RuClH(H_2)(PCy_3)_2$, which was prepared as described in Organometallics 1997, 16, 3867. The ligand exchange agent used was hexachloroethane. The acetylene used was phenylacetylene.

Example 21

Ring-Opening Cross Metathesis of Norbornadiene and 1-Decene. A 28.0 g (0.199 mol) amount of 1-decene was combined with 11.0 g (0.199 mol) of norbornadiene. A 6.8 mgs (9.8 μmol) amount of $RuClH(H_2)(PCy_3)_2$ was combined in a 20 ml vial with 140 mgs (60 equivalents) of hexachloroethane and 5.0 mgs (5 equivalents) of phenylacetylene in 1 ml of dichloromethane. The catalyst solution was combined into the 1-decene/norbornadiene mixture. An exotherm resulted. After one hour, the unreacted 1-decene and norbornadiene were removed via short path vacuum distillation. A 3.5 g amount of viscous oil remained and by $^1$H NMR was characterized as 1-decene capped oligomers of norbornadiene: $^1$H NMR δ 0.89 (t), 1.29 (m), 2.0 (m), 2.3 (m), 3.2 (br), 3.6 (br), 4.9-5.8 (multiplets); and as having >60% $C_{17}$ content by GC analysis.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise, "comprising" encompasses the terms "consisting essentially of," "is," and "consisting of" and anyplace "comprising" is used "consisting essentially of," "is," or "consisting of" may be substituted therefor.

What is claimed is:

1. A metathesis catalyst comprising:
   i. a Group 8 metal hydride-dihydrogen complex represented by the formula:

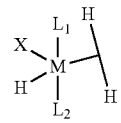

wherein
M is a Group 8 metal;
X is an anionic ligand; and
$L_1$ and $L_2$ are neutral donor ligands; and
   ii. a ligand exchange agent represented by the formula J-Y, wherein
J is selected from the group consisting of hydrogen, a $C_1$ to $C_{30}$ hydrocarbyl, and a $C_1$ to $C_{30}$ substituted hydrocarbyl; and
Y is selected from the group consisting of halides, alkoxides, aryloxides, and alkyl sulfonates.

2. The metathesis catalyst composition of claim 1, wherein M is ruthenium or osmium.

3. The metathesis catalyst composition of claim 1, wherein X is selected from the group consisting of halides, alkoxides, aryloxides, and alkyl sulfonates.

4. The metathesis catalyst composition of claim 1, wherein $L_1$ and $L_2$ are independently selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof.

5. The metathesis catalyst composition of claim 1, wherein at least one of $L_1$ and $L_2$ is selected from a phosphine, an N-heterocyclic carbene, a cyclic alkyl amino carbene, and substituted analogs thereof.

6. The metathesis catalyst composition of claim 1, wherein Y is a chloride group.

7. The metathesis catalyst composition of claim 1, wherein the Group 8 metal hydride-dihydrogen complex is selected from (1,3-bis-(2,4,6-trimethylphenyl)-2-(imidazolidinylidene)(tricyclohexylphosphine)(dihydrogen)rutheniumhydridochloride, bis-(tricyclohexylphosphine)(dihydrogen)rutheniumhydridochloride, (1-mesityl-3-methyl-2H-4,5-dihydroimidazol-2-ylidene)(tricyclohexylphosphine)-(dihydrogen)rutheniumhydridochloride, 2-(2,6-diethylphenyl)-3,3,5,5-tetramethylpyrrolidine-(tricyclohexylphosphine)-(dihydrogen)rutheniumhydridochloride.

8. The metathesis catalyst composition of claim 1, further comprising an acetylene compound represented by the formula:

wherein $R_1$ and $R_2$ are independently selected from the group consisting of hydrogen, a $C_1$ to $C_{30}$ hydrocarbyl, and a $C_1$ to $C_{30}$ substituted hydrocarbyl.

9. The metathesis catalyst composition of claim 8, wherein the ligand exchange agent is hexachloroethane and the acetylene compound is phenylacetylene.

10. A method for making a metathesis catalyst comprising:
contacting a Group 8 metal hydride-dihydrogen complex with a ligand exchange agent;
wherein the Group 8 metal hydride-dihydrogen complex is represented by the formula:

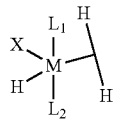

wherein
M is a Group 8 metal;
X is an anionic ligand; and
$L_1$ and $L_2$ are neutral donor ligands; and
wherein the ligand exchange agent is represented by the formula J-Y,
wherein
J is selected from the group consisting of hydrogen, a $C_1$ to $C_{30}$ hydrocarbyl, and a $C_1$ to $C_{30}$ substituted hydrocarbyl; and
Y is selected from the group consisting of halides, alkoxides, aryloxides, and alkyl sulfonates.

11. The method of claim 10, wherein M is ruthenium or osmium.

12. The method of claim 10, wherein X is selected from the group consisting of halides, alkoxides, aryloxides, and alkyl sulfonates.

13. The method of claim 10, wherein $L_1$ and $L_2$ are independently selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof.

14. The method of claim 10, wherein at least one of $L_1$ and $L_2$ is selected from a phosphine, an N-heterocyclic carbene, a cyclic alkyl amino carbene, and substituted analogs thereof.

15. The method of claim 10, wherein Y is a chloride group.

16. The method of claim 10, wherein the Group 8 metal hydride-dihydrogen complex is selected from (1,3-bis-(2,4,6-trimethylphenyl)-2-(imidazolidinylidene)(tricyclohexylphosphine)(dihydrogen)rutheniumhydridochloride, bis-(tricyclohexylphosphine)(dihydrogen)rutheniumhydridochloride, (1-mesityl-3-methyl-2H-4,5-dihydroimidazol-2-ylidene)(tricyclohexylphosphine)(dihydrogen)rutheniumhydridochloride, diethylphenyl)-3,3,5,5-tetramethylpyrrolidine(tricyclohexylphosphine)(dihydrogen)rutheniumhydridochloride.

17. The method of claim 10, further comprising contacting the Group 8 metal hydride-dihydrogen complex and the ligand exchange agent with an acetylene compound represented by the formula:

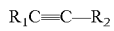

wherein $R_1$ and $R_2$ are independently selected from the group consisting of hydrogen, a $C_1$ to $C_{30}$ hydrocarbyl, and a $C_1$ to $C_{30}$ substituted hydrocarbyl.

18. The method of claim 17, wherein the ligand exchange agent is hexachloroethane and the acetylene compound is phenylacetylene.

19. A process for performing a metathesis reaction comprising:
contacting at least one olefin with a metathesis catalyst,
wherein the metathesis catalyst comprises a Group 8 metal hydride-dihydrogen complex represented by the formula:

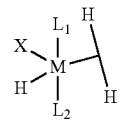

wherein
M is a Group 8 metal;
X is an anionic ligand; and
$L_1$ and $L_2$ are neutral donor ligands.

20. The process of claim 19, wherein M is ruthenium or osmium.

21. The process of claim 19, wherein X is selected from the group consisting of halides, alkoxides, aryloxides, and alkyl sulfonates.

22. The process of claim 19, wherein $L_1$ and $L_2$ are independently selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof.

23. The process of claim 19, wherein at least one of $L_1$ and $L_2$ is selected from a phosphine, an N-heterocyclic carbene, a cyclic alkyl amino carbene, and substituted analogs thereof.

24. The process of claim 19, wherein the Group 8 metal hydride-dihydrogen complex is selected from (1,3-bis-(2,4,6-trimethylphenyl)-2-(imidazolidinylidene)(tricyclohexylphosphine)(dihydrogen)rutheniumhydridochloride, bis-(tricyclohexylphosphine)(dihydrogen)rutheniumhydridochloride, (1-mesityl-3-methyl-2H-4,5-dihydroimidazol-2-ylidene)(tricyclohexylphosphine)-(dihydrogen)rutheniumhydridochloride, 2-(2,6-diethylphenyl)-3,3,5,5-tetramethylpyrrolidine(tricyclohexylphosphine)(dihydrogen)ruthenium hydridochloride.

25. A process for performing a metathesis reaction comprising:
contacting at least one olefin with a metathesis catalyst,
wherein the metathesis catalyst comprises: i) a Group 8 metal hydride-dihydrogen complex represented by the formula:

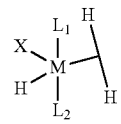

wherein
M is a Group 8 metal;
X is an anionic ligand; and
$L_1$ and $L_2$ are neutral donor ligands, (ii) a ligand exchange agent represented by the formula J-Y, wherein
J is selected from the group consisting of hydrogen, a $C_1$ to $C_{30}$ hydrocarbyl, and a $C_1$ to $C_{30}$ substituted hydrocarbyl; and
Y is selected from the group consisting of halides, alkoxides, aryloxides, and alkyl sulfonates.

26. The process of claim 25, wherein Y is a chloride.

27. The process of claim 25, wherein the metathesis catalyst further comprises an acetylene compound represented by the formula:

wherein $R_1$ and $R_2$ are independently selected from the group consisting of hydrogen, a $C_1$ to $C_{30}$ hydrocarbyl, and a $C_1$ to $C_{30}$ substituted hydrocarbyl.

28. The process of claim 27, wherein the ligand exchange agent is hexachloroethane and the acetylene compound is phenylacetylene.

29. The process of claim 19, wherein the at least one olefin comprises at least one renewable feedstream and at least one lower olefin having the formula $R^*$—HC=CH—$R^*$, wherein each $R^*$ is independently, hydrogen or a $C_1$ to $C_2$ hydrocarbyl.

30. The process of claim 29, wherein the at least one renewable feedstream is selected from canola oil, corn oil, soybean oil, rapeseed oil, algae oil, peanut oil, mustard oil, sunflower oil, tung oil, tall oil, perilla oil, grapeseed oil, linseed oil, safflower oil, pumpkin oil, palm oil, Jatropha oil, high-oleic soybean oil, high-oleic safflower oil, high-oleic sunflower oil, mixtures of animal and vegetable fats and oils, beef tallow, castor bean oil, dehydrated castor bean oil, cucumber oil, poppyseed oil, flaxseed oil, lesquerella oil, walnut oil, cottonseed oil, meadowfoam, tuna oil, sesame oils, waste oils/greases and mixtures thereof.

31. The process of claim 29, wherein the renewable feedstream is selected from palm oil, soybean oil, sunflower oil, canola oil, Jatropha oil, and algae oil.

32. The process of claim 29, wherein the at least one lower olefin is at least one of ethylene, propylene, butene, butadiene, and isomers thereof.

33. The process of claim 29, wherein a linear poly-alpha-olefin is produced.

34. The process of claim 19, wherein the at least one olefin comprises at least one cyclic olefin.

35. The process of claim 34, wherein the at least one cyclic olefin is selected from cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, and norbornadiene.

36. The process of claim 34, wherein a polyolefin is produced.

37. The process of claim 19, wherein the at least one olefin is a linear alpha olefin, and wherein the linear alpha olefin is isomerized to internal isomers thereof.

38. The process of claim 25, wherein M is ruthenium or osmium.

39. The process of claim 25, wherein X is selected from the group consisting of halides, alkoxides, aryloxides, and alkyl sulfonates.

40. The process of claim 25, wherein $L_1$ and $L_2$ are independently selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof.

41. The process of claim 25, wherein at least one of $L_1$ and $L_2$ is selected from a phosphine, an N-heterocyclic carbene, a cyclic alkyl amino carbene, and substituted analogs thereof.

42. The process of claim 25, wherein the Group 8 metal hydride-dihydrogen complex is selected from (1,3-bis-(2,4,6-trimethylphenyl)-2-(imidazolidinylidene)(tricyclohexylphosphine)(dihydrogen)rutheniumhydridochloride, bis-(tricyclohexylphosphine)(dihydrogen) rutheniumhydridochloride, (1-mesityl-3-methyl-2H-4,5-dihydroimidazol-2-ylidene)(tricyclohexylphosphine)-(dihydrogen)rutheniumhydridochloride, and 2-(2,6-diethylphenyl)-3,3,5,5-tetramethylpyrrolidine (tricyclohexylphosphine)(dihydrogen)ruthenium hydridochloride.

43. The process of claim 25, wherein the at least one olefin comprises at least one renewable feedstream and at least one lower olefin having the formula $R^*$—HC=CH—$R^*$, wherein each $R^*$ is independently hydrogen or a $C_1$ to $C_2$ hydrocarbyl.

44. The process of claim 43, wherein the at least one renewable feedstream is selected from canola oil, corn oil, soybean oil, rapeseed oil, algae oil, peanut oil, mustard oil, sunflower oil, tung oil, tall oil, perilla oil, grapeseed oil, linseed oil, safflower oil, pumpkin oil, palm oil, Jatropha oil, high-oleic soybean oil, high-oleic safflower oil, high-oleic sunflower oil, mixtures of animal and vegetable fats and oils, beef tallow, castor bean oil, dehydrated castor bean oil, cucumber oil, poppyseed oil, flaxseed oil, lesquerella oil, walnut oil, cottonseed oil, meadowfoam, tuna oil, sesame oils, waste oils/greases, and mixtures thereof.

45. The process of claim 43, wherein the renewable feedstream is selected from palm oil, soybean oil, sunflower oil, canola oil, Jatropha oil, and algae oil.

46. The process of claim 43, wherein the at least one lower olefin is at least one of ethylene, propylene, butene, butadiene, and isomers thereof.

47. The process of claim 43, wherein a linear poly-alpha-olefin is produced.

48. The process of claim 25, wherein the at least one olefin comprises at least one cyclic olefin.

49. The process of claim 48, wherein the at least one cyclic olefin is selected from cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, and norbornadiene.

50. The process of claim 48, wherein a polyolefin is produced.

51. The process of claim 25, wherein the at least one olefin is a linear alpha olefin, and wherein the linear alpha olefin is isomerized to internal isomers thereof.

* * * * *